(12) United States Patent
Van Hoven et al.

(10) Patent No.: US 11,590,321 B2
(45) Date of Patent: Feb. 28, 2023

(54) CATHETER GUIDING SYSTEM AND METHODS

(71) Applicant: Evalve, Inc., Santa Clara, CA (US)

(72) Inventors: Dylan T. Van Hoven, San Carlos, CA (US); Jose C. Vital, San Jose, CA (US); Amy Lee, Sunnyvale, CA (US)

(73) Assignee: EVALVE, INC., Santa Clara, CA (US)

( * ) Notice: Subject to any disclaimer, the term of this patent is extended or adjusted under 35 U.S.C. 154(b) by 873 days.

(21) Appl. No.: 16/459,163

(22) Filed: Jul. 1, 2019

(65) Prior Publication Data

US 2019/0321597 A1    Oct. 24, 2019

Related U.S. Application Data

(63) Continuation of application No. 14/744,415, filed on Jun. 19, 2015, now Pat. No. 10,376,673.

(51) Int. Cl.
*A61M 25/01* (2006.01)
*A61B 17/128* (2006.01)
(Continued)

(52) U.S. Cl.
CPC ..... *A61M 25/0147* (2013.01); *A61B 17/1285* (2013.01); *A61B 2017/00243* (2013.01);
(Continued)

(58) Field of Classification Search
CPC .............. A61M 25/01; A61M 25/0147; A61M 25/0138; A61M 2025/015;
(Continued)

(56) References Cited

U.S. PATENT DOCUMENTS 2,097,018 A    10/1937   Chamberlain
3,557,780 A    1/1971    Sato
(Continued)

FOREIGN PATENT DOCUMENTS

CN    1469724    1/2004
CN    2726560    9/2005
(Continued)

OTHER PUBLICATIONS

U.S. Appl. No. 14/216,787, filed Mar. 17, 2014, Basude et al.
(Continued)

*Primary Examiner* — Tiffany Legette
(74) *Attorney, Agent, or Firm* — Workman Nydegger

(57) ABSTRACT

A steerable guide catheter includes a tip ring at a distal end and one or more pullwires configured to engage with the tip ring when put in tension, the pullwire(s) thereby subjecting the steerable guide catheter to a curving or turning force. The tip ring includes a saddle and one or more pullwire channels allowing the pullwire to be looped over the saddle such that when the pullwire is placed under tension, it abuts against the saddle of the tip ring. Some embodiments include additional catheters axially aligned within or outside of the steerable guide catheter, and include a keying feature aligning the rotation of the multiple catheters. The keys of the keying feature can be formed of a polyamide with a glass microsphere filler, and can be thermally welded to the catheter.

20 Claims, 15 Drawing Sheets

(51) Int. Cl.
*A61B 17/00* (2006.01)
*A61M 25/00* (2006.01)

(52) U.S. Cl.
CPC .............. *A61B 2017/00318* (2013.01); *A61B 2017/00783* (2013.01); *A61M 2025/0004* (2013.01); *A61M 2025/015* (2013.01)

(58) Field of Classification Search
CPC .... A61B 2017/003; A61B 2017/00243; A61B 2017/00314; A61B 2017/00323; A61B 2017/00318; A61B 17/00234; A61B 17/1285
See application file for complete search history.

(56) References Cited

U.S. PATENT DOCUMENTS

| | | |
|---|---|---|
| 3,671,979 A | 6/1972 | Moulopoulos |
| 4,406,656 A | 9/1983 | Hattler et al. |
| 4,484,579 A | 11/1984 | Meno et al. |
| 4,510,934 A | 4/1985 | Batra |
| 4,578,061 A | 3/1986 | Lemelson |
| 4,641,366 A | 2/1987 | Yokoyama et al. |
| 4,686,965 A | 8/1987 | Bonnet et al. |
| 4,777,951 A | 10/1988 | Cribier et al. |
| 4,896,986 A | 1/1990 | Terayama |
| 4,969,890 A | 11/1990 | Sugita et al. |
| 5,042,161 A | 8/1991 | Hodge |
| 5,042,707 A | 8/1991 | Taheri |
| 5,108,368 A | 4/1992 | Hammerslag et al. |
| 5,190,554 A | 3/1993 | Coddington et al. |
| 5,195,968 A | 3/1993 | Lundquist et al. |
| 5,236,450 A | 8/1993 | Scott |
| 5,251,611 A | 10/1993 | Zehel et al. |
| 5,263,939 A | 11/1993 | Wortrich |
| 5,289,831 A * | 3/1994 | Bosley .................. A61B 90/39 128/899 |
| 5,304,131 A | 4/1994 | Paskar |
| 5,312,415 A | 5/1994 | Palermo |
| 5,318,525 A | 6/1994 | West et al. |
| 5,325,845 A | 7/1994 | Adair |
| 5,345,945 A | 9/1994 | Hodgson et al. |
| 5,359,994 A | 11/1994 | Kreuter et al. |
| 5,368,564 A | 11/1994 | Savage |
| 5,403,326 A | 4/1995 | Harrison et al. |
| 5,405,402 A | 4/1995 | Dye et al. |
| 5,417,699 A | 5/1995 | Klein et al. |
| 5,462,527 A | 10/1995 | Stevens-Wright et al. |
| 5,464,394 A | 11/1995 | Miller et al. |
| 5,472,044 A | 12/1995 | Hall et al. |
| 5,472,423 A | 12/1995 | Gronauer |
| 5,478,309 A | 12/1995 | Sweezer et al. |
| 5,489,296 A | 2/1996 | Love et al. |
| 5,507,725 A | 4/1996 | Savage et al. |
| 5,571,085 A | 11/1996 | Accisano, III |
| 5,630,832 A | 5/1997 | Giordano et al. |
| 5,662,606 A | 9/1997 | Cimino et al. |
| 5,669,919 A | 9/1997 | Sanders et al. |
| 5,706,824 A | 1/1998 | Whittier |
| 5,715,817 A | 2/1998 | Stevens-Wright et al. |
| 5,716,367 A | 2/1998 | Koike et al. |
| 5,718,714 A | 2/1998 | Livneh |
| 5,718,725 A | 2/1998 | Sterman et al. |
| 5,729,646 A * | 3/1998 | Miyagi .................. G02B 6/102 385/125 |
| 5,738,649 A | 4/1998 | Macoviak |
| 5,741,286 A | 4/1998 | Recuset |
| 5,749,828 A | 5/1998 | Solomon et al. |
| 5,769,812 A | 6/1998 | Stevens et al. |
| 5,772,578 A | 6/1998 | Heimberger et al. |
| 5,810,849 A | 9/1998 | Kontos |
| 5,810,876 A | 9/1998 | Kelleher |
| 5,814,029 A | 9/1998 | Hassett |
| 5,820,591 A | 10/1998 | Thompson et al. |
| 5,820,592 A | 10/1998 | Hammerslag |
| 5,823,955 A | 10/1998 | Kuck et al. |
| 5,833,671 A | 11/1998 | Macoviak et al. |
| 5,843,103 A | 12/1998 | Wulfman |
| 5,855,590 A | 1/1999 | Malecki et al. |
| 5,871,493 A | 2/1999 | Sjostrom et al. |
| 5,902,290 A | 5/1999 | Peacock, III et al. |
| 5,916,147 A | 6/1999 | Boury |
| 5,957,973 A | 9/1999 | Quiachon et al. |
| 5,964,717 A | 10/1999 | Gottlieb et al. |
| 5,993,470 A | 11/1999 | Yoon |
| 6,033,378 A | 3/2000 | Lundquist et al. |
| 6,066,126 A | 5/2000 | Li et al. |
| 6,068,629 A | 5/2000 | Haissaguerre et al. |
| 6,086,600 A | 7/2000 | Kortenbach |
| 6,090,118 A | 7/2000 | McGuckin, Jr. |
| 6,123,699 A | 9/2000 | Webster, Jr. |
| 6,139,214 A | 10/2000 | Zirps et al. |
| 6,180,059 B1 | 1/2001 | Divino, Jr. et al. |
| 6,312,447 B1 | 11/2001 | Grimes |
| 6,319,250 B1 | 11/2001 | Falwell et al. |
| 6,350,281 B1 | 2/2002 | Rhee |
| 6,419,669 B1 | 7/2002 | Frazier et al. |
| 6,461,366 B1 | 10/2002 | Seguin |
| 6,482,224 B1 | 11/2002 | Michler et al. |
| 6,517,550 B1 | 2/2003 | Konya et al. |
| 6,540,755 B2 | 4/2003 | Ockuly et al. |
| 6,629,534 B1 | 10/2003 | St. Goar et al. |
| 6,685,648 B2 | 2/2004 | Flaherty et al. |
| 6,702,825 B2 | 3/2004 | Frazier et al. |
| 6,752,813 B2 | 6/2004 | Goldfarb et al. |
| 6,770,083 B2 | 8/2004 | Seguin |
| 6,926,725 B2 | 8/2005 | Cooke et al. |
| 6,945,978 B1 | 9/2005 | Hyde |
| 7,226,467 B2 * | 6/2007 | Lucatero .............. A61B 17/0487 606/191 |
| 7,288,097 B2 | 10/2007 | Seguin |
| 7,291,168 B2 | 11/2007 | Macoviak et al. |
| 7,381,210 B2 | 6/2008 | Zarbatany et al. |
| 7,563,267 B2 | 7/2009 | Goldfarb et al. |
| 7,655,015 B2 | 2/2010 | Goldfarb et al. |
| 7,666,204 B2 | 2/2010 | Thornton et al. |
| 8,216,256 B2 | 7/2012 | Raschdorf, Jr. et al. |
| D668,334 S | 10/2012 | Makowski et al. |
| 8,523,881 B2 | 9/2013 | Cabiri et al. |
| 8,647,323 B2 | 2/2014 | Guo et al. |
| 8,926,588 B2 | 1/2015 | Berthiaume et al. |
| D740,414 S | 10/2015 | Katsura |
| 9,700,445 B2 | 7/2017 | Martin et al. |
| D809,139 S | 1/2018 | Marsot et al. |
| 10,376,673 B2 | 8/2019 | Van Hoven et al. |
| 10,413,408 B2 | 9/2019 | Krone et al. |
| 2001/0002445 A1 | 5/2001 | Vesely |
| 2001/0005787 A1 | 6/2001 | Oz et al. |
| 2001/0007067 A1 | 7/2001 | Kurfess et al. |
| 2001/0037084 A1 | 11/2001 | Nardeo |
| 2002/0013547 A1 | 1/2002 | Paskar |
| 2002/0013571 A1 | 1/2002 | Goldfarb et al. |
| 2002/0035361 A1 | 3/2002 | Houser et al. |
| 2002/0058910 A1 | 5/2002 | Hermann et al. |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0147456 A1 | 10/2002 | Diduch et al. |
| 2002/0156526 A1 | 10/2002 | Hilavka et al. |
| 2002/0169377 A1 | 11/2002 | Khairkhahan et al. |
| 2003/0045778 A1 | 3/2003 | Ohline et al. |
| 2003/0114832 A1 | 6/2003 | Kohler et al. |
| 2003/0120341 A1 | 6/2003 | Shennib et al. |
| 2003/0130730 A1 | 7/2003 | Cohn et al. |
| 2003/0181855 A1 | 9/2003 | Simpson et al. |
| 2003/0187467 A1 | 10/2003 | Schreck |
| 2003/0208231 A1 | 11/2003 | Williamson, IV et al. |
| 2003/0233038 A1 | 12/2003 | Hassett |
| 2004/0002719 A1 | 1/2004 | Oz et al. |
| 2004/0003819 A1 | 1/2004 | St. Goar et al. |
| 2004/0019377 A1 | 1/2004 | Taylor et al. |
| 2004/0024414 A1 | 2/2004 | Downing |
| 2004/0030382 A1 | 2/2004 | St. Goar et al. |
| 2004/0039442 A1 | 2/2004 | St. Goar et al. |

(56) References Cited

U.S. PATENT DOCUMENTS

| | | |
|---|---|---|
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0087975 A1* | 5/2004 | Lucatero ............ A61B 17/0469 |
| | | 606/139 |
| 2004/0088047 A1 | 5/2004 | Spence et al. |
| 2004/0092962 A1 | 5/2004 | Thorton et al. |
| 2004/0116848 A1 | 6/2004 | Gardeski et al. |
| 2004/0127849 A1 | 7/2004 | Kantor |
| 2004/0133192 A1 | 7/2004 | Houser et al. |
| 2004/0133220 A1 | 7/2004 | Lashinski et al. |
| 2004/0133232 A1 | 7/2004 | Rosenbluth et al. |
| 2004/0133240 A1 | 7/2004 | Adams et al. |
| 2004/0138529 A1 | 7/2004 | Wiltshire et al. |
| 2004/0138675 A1 | 7/2004 | Crabtree |
| 2004/0138744 A1 | 7/2004 | Lashinski et al. |
| 2004/0138745 A1 | 7/2004 | Macoviak et al. |
| 2004/0147826 A1 | 7/2004 | Peterson |
| 2004/0153144 A1 | 8/2004 | Seguin |
| 2004/0158123 A1 | 8/2004 | Jayaraman |
| 2004/0162610 A1 | 8/2004 | Laiska et al. |
| 2004/0186486 A1 | 9/2004 | Roue et al. |
| 2004/0193191 A1 | 9/2004 | Starksen et al. |
| 2004/0199052 A1 | 10/2004 | Banik et al. |
| 2004/0225300 A1 | 11/2004 | Goldfarb et al. |
| 2004/0236354 A1 | 11/2004 | Seguin |
| 2004/0243227 A1 | 12/2004 | Starksen et al. |
| 2004/0249453 A1 | 12/2004 | Cartledge et al. |
| 2005/0006432 A1 | 1/2005 | Racenet et al. |
| 2005/0021056 A1 | 1/2005 | St. Goer et al. |
| 2005/0021057 A1 | 1/2005 | St. Goer et al. |
| 2005/0033446 A1 | 2/2005 | Deem et al. |
| 2005/0038383 A1 | 2/2005 | Kelley et al. |
| 2005/0059351 A1 | 3/2005 | Cauwels et al. |
| 2005/0085903 A1 | 4/2005 | Lau |
| 2005/0143809 A1 | 6/2005 | Salahieh et al. |
| 2005/0216039 A1 | 9/2005 | Lederman |
| 2005/0228422 A1 | 10/2005 | Machold et al. |
| 2005/0251001 A1 | 11/2005 | Hassett |
| 2005/0256452 A1 | 11/2005 | DeMarchi et al. |
| 2005/0267493 A1 | 12/2005 | Schreck et al. |
| 2005/0277874 A1 | 12/2005 | Selkee |
| 2005/0277876 A1 | 12/2005 | Hayden |
| 2006/0009715 A1 | 1/2006 | Khairkhahan et al. |
| 2006/0030866 A1 | 2/2006 | Schreck |
| 2006/0030867 A1 | 2/2006 | Zadno |
| 2006/0030885 A1 | 2/2006 | Hyde |
| 2006/0064115 A1 | 3/2006 | Allen et al. |
| 2006/0064116 A1 | 3/2006 | Allen et al. |
| 2006/0074484 A1 | 4/2006 | Huber |
| 2006/0135961 A1 | 6/2006 | Rosenman et al. |
| 2006/0135993 A1 | 6/2006 | Seguin |
| 2006/0184203 A1 | 8/2006 | Martin et al. |
| 2006/0229708 A1 | 10/2006 | Powell et al. |
| 2006/0252984 A1 | 11/2006 | Randert et al. |
| 2006/0287643 A1 | 12/2006 | Perlin |
| 2007/0038293 A1 | 2/2007 | St. Goar et al. |
| 2007/0060997 A1 | 3/2007 | de Boer |
| 2007/0088277 A1 | 4/2007 | McGinley et al. |
| 2007/0088431 A1 | 4/2007 | Bourang et al. |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0156225 A1 | 7/2007 | George et al. |
| 2007/0173757 A1 | 7/2007 | Levine et al. |
| 2007/0197858 A1 | 8/2007 | Goldfarb et al. |
| 2007/0198082 A1 | 8/2007 | Kapadia et al. |
| 2007/0260225 A1 | 11/2007 | Sakakine et al. |
| 2008/0051703 A1 | 2/2008 | Thorton et al. |
| 2008/0051807 A1 | 2/2008 | St. Goar et al. |
| 2008/0097489 A1 | 4/2008 | Goldfarb et al. |
| 2008/0154299 A1 | 6/2008 | Livneh |
| 2008/0167714 A1 | 7/2008 | St. Goer et al. |
| 2008/0183194 A1 | 7/2008 | Goldfarb et al. |
| 2008/0188850 A1 | 8/2008 | Mody et al. |
| 2008/0195126 A1 | 8/2008 | Solem |
| 2008/0287741 A1 | 11/2008 | Ostrovsky et al. |
| 2009/0036768 A1 | 2/2009 | Seehusen et al. |
| 2009/0099554 A1 | 4/2009 | Forster et al. |
| 2009/0143851 A1 | 6/2009 | Paul, Jr. |
| 2009/0156995 A1 | 6/2009 | Martin et al. |
| 2009/0163934 A1 | 6/2009 | Raschdorf, Jr. et al. |
| 2009/0198322 A1 | 8/2009 | Deem et al. |
| 2009/0201172 A1* | 8/2009 | Edell .................. A61B 5/0002 |
| | | 600/300 |
| 2009/0204005 A1 | 8/2009 | Keast et al. |
| 2009/0270858 A1 | 10/2009 | Hauck et al. |
| 2009/0276039 A1 | 11/2009 | Meretei |
| 2009/0281619 A1 | 11/2009 | Le et al. |
| 2009/0326567 A1 | 12/2009 | Goldfarb et al. |
| 2010/0016958 A1 | 1/2010 | St. Goer et al. |
| 2010/0022823 A1 | 1/2010 | Goldfarb et al. |
| 2010/0044410 A1 | 2/2010 | Argentine et al. |
| 2010/0070050 A1* | 3/2010 | Mathis .................. A61B 5/091 |
| | | 623/23.65 |
| 2010/0168717 A1 | 7/2010 | Grasse et al. |
| 2010/0217184 A1 | 8/2010 | Koblish et al. |
| 2010/0217261 A1 | 8/2010 | Watson |
| 2010/0252293 A1 | 10/2010 | Lopano et al. |
| 2010/0324370 A1 | 12/2010 | Dohi et al. |
| 2010/0331776 A1 | 12/2010 | Salahieh et al. |
| 2011/0077498 A1 | 3/2011 | McDaniel |
| 2011/0190778 A1 | 8/2011 | Arpasi et al. |
| 2011/0208169 A1 | 8/2011 | Nash |
| 2012/0022640 A1 | 1/2012 | Gross et al. |
| 2012/0065464 A1 | 3/2012 | Ellis et al. |
| 2012/0089136 A1 | 4/2012 | Levin et al. |
| 2012/0172915 A1 | 7/2012 | Fifer et al. |
| 2012/0253329 A1 | 10/2012 | Zemlok et al. |
| 2012/0316639 A1 | 12/2012 | Kleinschrodt |
| 2012/0330348 A1 | 12/2012 | Strauss et al. |
| 2012/0330408 A1 | 12/2012 | Hillukka et al. |
| 2013/0041314 A1 | 2/2013 | Dillon |
| 2013/0053822 A1 | 2/2013 | Fischell et al. |
| 2013/0066342 A1 | 3/2013 | Dell et al. |
| 2013/0304117 A1 | 11/2013 | Sugiyama |
| 2013/0310813 A1 | 11/2013 | Kaercher et al. |
| 2014/0012287 A1 | 1/2014 | Oyola et al. |
| 2014/0025103 A1 | 1/2014 | Hundertmark et al. |
| 2014/0088358 A1* | 3/2014 | Banik .................... A61B 1/008 |
| | | 600/141 |
| 2014/0148651 A1 | 5/2014 | Aman et al. |
| 2014/0148673 A1 | 5/2014 | Bogusky |
| 2014/0171923 A1 | 6/2014 | Aranyi |
| 2014/0180124 A1 | 6/2014 | Whiseant et al. |
| 2014/0196923 A1 | 7/2014 | Leupert et al. |
| 2014/0243969 A1 | 8/2014 | Venkatasubramanian et al. |
| 2014/0276966 A1 | 9/2014 | Ranucci et al. |
| 2014/0324164 A1 | 10/2014 | Gross et al. |
| 2015/0005704 A1 | 1/2015 | Heisel et al. |
| 2015/0005801 A1 | 1/2015 | Marquis et al. |
| 2015/0024053 A1* | 1/2015 | Harrison ................ A61K 45/06 |
| | | 514/588 |
| 2015/0060516 A1 | 3/2015 | Collings et al. |
| 2015/0112430 A1 | 4/2015 | Creaven et al. |
| 2015/0182334 A1 | 7/2015 | Bourang et al. |
| 2015/0211946 A1 | 7/2015 | Pons et al. |
| 2015/0272759 A1 | 10/2015 | Argentine |
| 2015/0306806 A1 | 10/2015 | Dando et al. |
| 2016/0174979 A1 | 6/2016 | Wei |
| 2016/0228247 A1 | 8/2016 | Maimon et al. |
| 2016/0374811 A1 | 12/2016 | McNiven et al. |
| 2017/0042678 A1 | 2/2017 | Ganesan et al. |
| 2017/0080186 A1 | 3/2017 | Salahieh et al. |
| 2017/0100250 A1 | 4/2017 | Marsot et al. |
| 2017/0128205 A1 | 5/2017 | Tamir et al. |
| 2017/0224319 A1 | 8/2017 | Martin et al. |
| 2017/0232238 A1 | 8/2017 | Biller et al. |
| 2018/0028215 A1 | 2/2018 | Cohen |
| 2018/0360457 A1 | 12/2018 | Ellis et al. |

(56) References Cited

U.S. PATENT DOCUMENTS

| | | |
|---|---|---|
| 2019/0030285 A1 | 1/2019 | Prabhu et al. |
| 2020/0121894 A1 | 4/2020 | Prabhu et al. |

FOREIGN PATENT DOCUMENTS

| | | |
|---|---|---|
| CN | 101309654 | 11/2008 |
| CN | 102770080 | 11/2012 |
| CN | 103841899 | 6/2014 |
| CN | 102258402 | 11/2014 |
| DE | 3504292 | 7/1986 |
| EP | 0782836 | 7/1997 |
| EP | 0990449 | 4/2000 |
| EP | 1674040 | 6/2006 |
| EP | 1980288 | 10/2008 |
| EP | 2465568 | 6/2012 |
| EP | 2537487 | 12/2012 |
| EP | 2702965 | 3/2014 |
| EP | 3009103 | 4/2016 |
| FR | 2768324 | 3/1999 |
| GB | 2222951 | 3/1990 |
| JP | 2006528911 | 12/2006 |
| JP | 2013516244 | 5/2013 |
| JP | 2014523274 | 9/2014 |
| WO | WO 1997018746 | 5/1997 |
| WO | WO 1997038748 | 10/1997 |
| WO | WO 1997039688 | 10/1997 |
| WO | WO 1997048436 | 12/1997 |
| WO | WO 1998007375 | 2/1998 |
| WO | WO 1999013777 | 3/1999 |
| WO | WO 2000003651 | 1/2000 |
| WO | WO 2000012168 | 3/2000 |
| WO | 00/60995 A2 | 10/2000 |
| WO | WO 2001000114 | 1/2001 |
| WO | WO 2001028432 | 4/2001 |
| WO | WO 2001047438 | 7/2001 |
| WO | WO 2001070320 | 9/2001 |
| WO | WO 2001089440 | 11/2001 |
| WO | WO 2002060352 | 8/2002 |
| WO | WO 2002062263 | 8/2002 |
| WO | WO 2002062270 | 8/2002 |
| WO | WO 2002062408 | 8/2002 |
| WO | WO 2003001893 | 1/2003 |
| WO | WO 2003003930 | 1/2003 |
| WO | WO 2003020179 | 3/2003 |
| WO | WO 2003049619 | 6/2003 |
| WO | WO 2004012583 | 2/2004 |
| WO | WO 2004012789 | 2/2004 |
| WO | WO 2004037317 | 5/2004 |
| WO | WO 2004045378 | 6/2004 |
| WO | WO 2004045463 | 6/2004 |
| WO | WO 2004082523 | 9/2004 |
| WO | WO 2004103162 | 12/2004 |
| WO | WO 2005018507 | 3/2005 |
| WO | WO 2005062931 | 7/2005 |
| WO | WO 2005112792 | 12/2005 |
| WO | WO 2006105008 | 10/2006 |
| WO | WO 2006105009 | 10/2006 |
| WO | WO 2007047488 | 4/2007 |
| WO | WO 2007136829 | 11/2007 |
| WO | WO 2008031103 | 3/2008 |
| WO | WO 2008103722 | 8/2008 |
| WO | WO 2010024801 | 3/2010 |
| WO | WO 2010121076 | 10/2010 |
| WO | 2011/082350 A1 | 7/2011 |
| WO | WO 2012020521 | 2/2012 |
| WO | 2012/151543 A1 | 11/2012 |
| WO | WO 2012151396 | 11/2012 |
| WO | WO 2014064694 | 5/2014 |
| WO | WO 2014121280 | 8/2014 |
| WO | WO 2014182797 | 11/2014 |
| WO | WO 2015061052 | 4/2015 |
| WO | WO 2016022797 | 2/2016 |
| WO | WO 2016144708 | 9/2016 |
| WO | WO 2016150806 | 9/2016 |
| WO | WO 2016204954 | 12/2016 |
| WO | WO 2017003606 | 1/2017 |
| WO | WO 2017023534 | 2/2017 |

OTHER PUBLICATIONS

U.S. Appl. No. 29/633,930, filed Jan. 17, 2018, Marsot et al.
Bernal et al., "The Valve Racket: a new and different concept of atrioventricular valve repair," Eur. J. Cardio-thoracic Surgery 29:1026-1029 (2006).
Chinese Office Action issued in Chinese Application No. 200980158707.2 dated Sep. 9, 2013.
Communication dated Apr. 28, 2017 issued by the European Patent Office in counterpart application No. 16196023.2.
Communication dated Jan. 26, 2017, from the European Patent Office in counterpart European application No. 16196023.2.
Communication dated May 8, 2017, from the European Patent Office in counterpart European Application No. 04752714.8.
Extended European Search Report, dated Oct. 17, 2014, issued in European Patent Application No. 06751584.1.
McCarthy et al., "Partial left ventriculectomy and mitral valve repair for end-stage congestive heart failure," European Journal of Cardio-thoracic Surgery, 13:337-343 (1998).
Modulus of Elasticity—Young Modulus for some common Materials, http://www.bestech.com.au/wp-content/uploads/Modulus-of-Elasticity.pdf, Jan. 16, 2018.
Patel et al., #57 Epicardial Atrial Defibrillation: Novel Treatment of Postoperative Atrial Fibrillation, 2003 STS Presentation, [Abstract Only].
Takizawa H et al: "Development of a microfine active bending catheter equipped with MIF tactile sensors", Micro Electro Mechanical Systems, 1999. MEMS '99. Twelfth IEEE International Conference on Orlando, FL, USA Jan. 17-21, 1999, Piscataway, NJ, USA,IEEE, US, Jan. 17, 1999 (Jan. 17, 1999), pp. 412-417, XP010321677, ISBN: 978-0-7803-5194-3, figures 1-3.
Tamura et al., "Edge to Edge Repair for Mitral Regurgitation in a Patient with Chronic Hemodialysis: Report of A Case," Kyobu Geka. The Japanese Journal of Thoracic Surgery, 54(9):788-790 (2001).
Tibayan et al., #59 Annular Geometric Remodeling in Chronic Ischemic Mitral Regurgitation, 2003 STS Presentation, [Abstract Only].
Umana et al., "'Bow-tie' Mitral Valve Repair Successfully Addresses Subvalvular Dysfunction in Ischemic Mitral Regurgitation," Surgical Forum, XLVIII:279-280 (1997).
U.S. Appl. No. 14/577,852, Oct. 20, 2016, Office Action.
U.S. Appl. No. 14/577,852, May 16, 2017, Office Action.
U.S. Appl. No. 14/577,852, Sep. 7, 2017, Office Action.
U.S. Appl. No. 14/577,852, Apr. 25, 2018, Notice of Allowance.
U.S. Appl. No. 14/744,415, Nov. 22, 2017, Office Action.
U.S. Appl. No. 14/744,415, Jun. 1, 2018, Office Action.
U.S. Appl. No. 14/744,415, Jan. 4, 2019, Office Action.
U.S. Appl. No. 14/744,415, Apr. 2, 2019, Notice of Allowance.
U.S. Appl. No. 14/754,274, Mar. 23, 2017, Restriction Requirement.
U.S. Appl. No. 14/754,274, May 26, 2017, Office Action.
U.S. Appl. No. 14/754,274, Dec. 4, 2017, Office Action.
U.S. Appl. No. 14/754,274, May 31, 2018, Office Action.
U.S. Appl. No. 14/754,274, Nov. 21, 2018, Notice of Allowance.
U.S. Appl. No. 14/820,141, Jan. 25, 2018, Office Action.
U.S. Appl. No. 14/820,141, Sep. 5, 2018, Office Action.
U.S. Appl. No. 14/820,141, Oct. 30, 2018, Interview Summary.
U.S. Appl. No. 14/820,141, Dec. 31, 2018, Office Action.
U.S. Appl. No. 14/820,141, May 14, 2019, Notice of Allowance.
U.S. Appl. No. 14/879,726, Oct. 2, 2017, Office Action.
U.S. Appl. No. 14/879,726, Apr. 20, 2018, Office Action.
U.S. Appl. No. 14/879,726, Sep. 5, 2018, Notice of Allowance.
U.S. Appl. No. 14/879,726, Nov. 8, 2018, Notice of Allowance.
U.S. Appl. No. 15/662,084, May 30, 2019, Office Action.
U.S. Appl. No. 15/662,084, Sep. 25, 2019, Office Action.
U.S. Appl. No. 29/505,404, Jan. 3, 2017, Restriction Requirement.
U.S. Appl. No. 29/505,404, Mar. 30, 2017, Office Action.
U.S. Appl. No. 29/505,404, Sep. 26, 2017, Notice of Allowance.

(56) References Cited

OTHER PUBLICATIONS

"Diving watch", Sep. 25, 2014, Retrieved from https://en.wikipedia.org/w/index.php?title=Diving_watch&oldid=627082924, Retrieved on Apr. 28, 2016, Chapter: Elapsed time controller pp. 1-13.

Bhudia et al., "Edge-to-Edge (Alfieri) Mitral Repair: Results in Diverse Clinical Settings," Ann Thorac Surg, 77:1598-1606 (2004).

FDA premarket approval—MitraClip Clip delivery system, Oct. 24, 2013, Retrieved from http://www.accessdata.fda.gov/cdrh.sub.-docs/pdf10/p100009a.pdf, Retrieved on Apr. 28, 2016, pp. 1-5.

Frazier et al., "Early Clinical Experience with an Implantable, Intracardiac Circulatory Support Device: Operative Considerations and Physiologic Implications," http://v.'\vw.sts.org/doc/7007 accessed on Sep. 24, 2008.

Gupta et al., "Influence of Older Donor Grafts on Heart Transplant Survival: Lack of Recipient Effects," http://wvrw.sts.org/doc/7007 accessed on Sep. 24, 2008.

Leitgeb, "Safety of Electromedical Devices: Law—Risks—Opportunities," May 6, 2010, Springer Science & Business Media ISBN: 978-3-21 1-99682-9, Retrieved from https://books.google.de, Retrieved on Apr. 28, 2016, pp. 66.

Notice of Allowance received for U.S. Appl. No. 14/754,274, dated Dec. 17, 2018.

Notice of Allowance received for U.S. Appl. No. 14/879,726, dated Dec. 26, 2018.

Patel et al., "Epicardial Atrial Defibrillation: Novel Treatment of Postoperative Atrial Fibrillation," http://www.sts.org/doc/7007 accessed on Sep. 23, 2008.

Robicsek et al., "The Bicuspid Aortic Valve. How Does It Function? Why Does It Fail," htt12://v-/Wvv-.sts.org/doc/7007 accessed on Sep. 24, 2008.

Tibayan et al., "Annular Geometric Remodeling m Chronic Ischemic Mitral Regurgitation," http://www.sts.org/doc/7007 accessed on Sep. 24, 2008.

U.S. Appl. No. 14/532,494, Aug. 19, 2016, Office Action.

U.S. Appl. No. 14/532,494, dated Dec. 19, 2016, Office Action.

U.S. Appl. No. 14/532,494, dated Mar. 10, 2017, Notice of Allowance.

Uchida et al, Percutaneous Cardiomyotomy and Valvulotomy with Angioscopic Guidance, Am. Heart J., Apr. 1991, pp. 1221-1224, vol. 121.

MitraClip Clip Delivery System IFU Instructions For Use, Mitraclip System, Steerable Guide Catheter Ref No. SGC01ST, Clip Delivery System Ref. No. CDS02ST, Mitraclip System Accessories, Stabilizer Ref No. SZR01ST, Support Plate Ref No. PLT01ST. Abbott Vascular, Evalve Inc. 2012.

\* cited by examiner

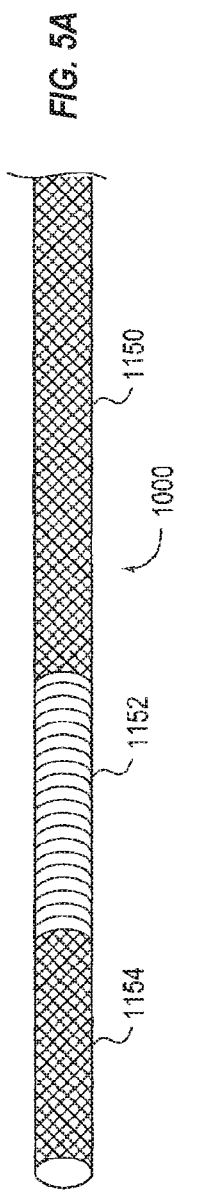
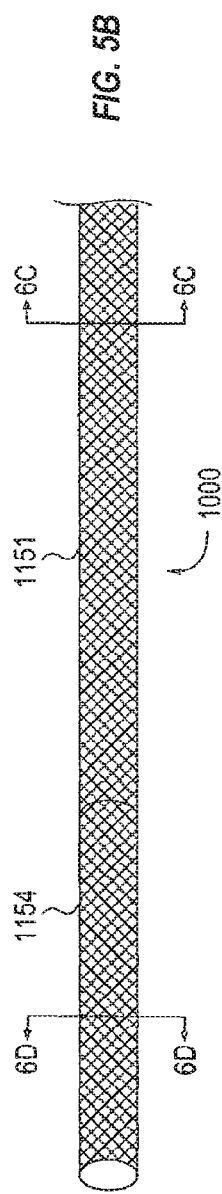
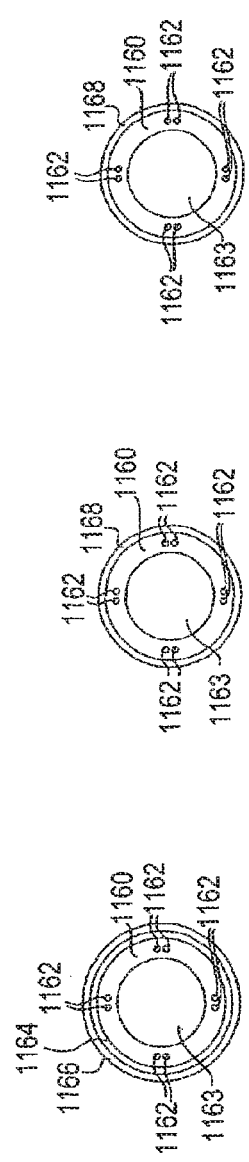
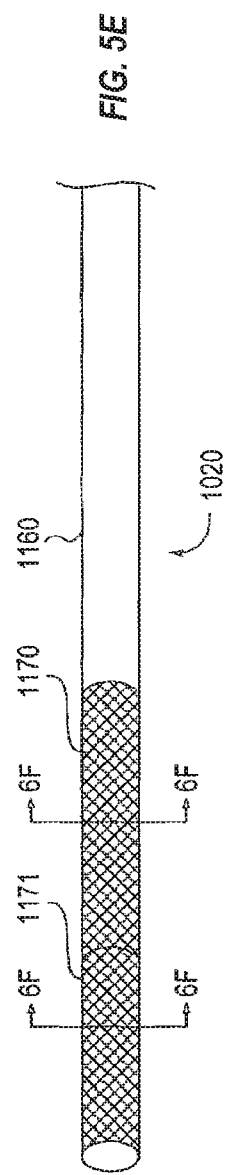

CATHETER GUIDING SYSTEM AND METHODS

CROSS-REFERENCE TO RELATED APPLICATIONS

This application is a continuation of U.S. patent application Ser. No. 14/744,415, filed Jun. 19, 2015, the entire contents of which is incorporated by reference herein.

BACKGROUND

The present invention relates to a guiding system for accessing a body cavity and directing the passage of devices therethrough into the cavity. Particularly, the present invention relates to a steerable catheter guiding system which directs the devices into the cavity in a desired orientation. In some embodiments, the present invention relates to endoluminally or transthoracically accessing an atrium of the heart to direct an interventional catheter toward a cardiac valve.

To access a target location within the human body from a remote location, a catheter is typically passed through one or more body lumens, such as through the vascular system, to the target location. When the vascular system is used, the catheter is inserted into an artery or vein percutaneously or through a relatively small incision in the patient's body. The catheter is then threaded through the patient's system of blood vessels to reach the desired target area. Often a pathway is created through the vasculature to the target location with the use of an introducer sheath. The sheath is slipped over a dilator or obturator which is advanced to the target location. The dilator or obturator is then removed and the sheath remains in place for use as a conduit for a variety of medical devices to access the target location. Such devices may include surgical instruments, fiber optic cables for visualization, lasers, electronic devices, or sensors capable of monitoring physiological parameters in situ to name a few. Although such access reduces the need for traditional invasive surgery, challenges arise related to control, manipulation, and positioning of instruments near the target location, particularly within a target body cavity.

Since cavities comprise open spaces, a device advanced to the cavity will typically protrude into the cavity at the angle in which it entered. If the target tissue is not within this pathway, the device will need to be steered toward the target tissue. If more than one device is used during a procedure, each device will need to be steered and repositioned when used. This increases the time and cost of the procedure and also the risk of misalignment.

For example, to gain access to the left atrium of the heart, the catheter and/or access sheath may be tracked from a puncture in the femoral vein, through the inferior vena cava, into the right atrium and through a puncture in the intra-atrial septum to the left atrium. When done for the purpose of mitral valve repair, this pathway may then be used to access the mitral valve which lies between the left atrium and the left ventricle. Since the mitral valve is located below the point of entry into the left atrium, devices which are inserted will need to be directed downward after entry, toward the mitral valve. In addition, devices used for applying interventional therapies to the mitral valve may require precise alignment with the valve commissures, leaflets, or coaptation line to perform the procedure. The devices may also be directed through the valve chordae or papillary muscles, for example, for interventional therapy to the mitral valve. When such procedures require the use of more than one instrument, each instrument would be dependent upon proper positioning in relation to the valve. This would require that positioning or steering mechanisms be built into each instrument and each instrument would be required to be properly positioned when introduced. This adds cost, complexity, and time to the overall procedure.

In other examples, the catheter and/or access sheath may also be tracked from a puncture in the femoral vein through the intra-atrial septum to the left atrium. This pathway may be used to access the left atrium for ablation of the atrium wall or ablation around the pulmonary veins. Such interventional therapies would require precise alignment with target areas for proper ablation placement. It may further be appreciated that alternative access routes may be desired to alternative body cavities. In any case, many of the same obstacles are encountered.

To overcome some of these challenges, pre-shaped access sheaths have been developed to direct instruments that are passed therethrough. For example, an access sheath having a pre-shaped curve at its distal end has been developed to both assist in negotiating twists and branches common in a patient's arterial or venous system and to maintain a shape once positioned within a target cavity. Since the pre-shaped curve is fixed into the access sheath at the time of manufacture, the radius, extent of the curvature and overall shape generally cannot be altered. Due to anatomical variations, extensive pre-surgical planning would be necessary to determine the correct curvature of the access sheath. Such tailoring would be prohibitively complex and a single predicted curvature would most likely still require additional repositioning once inside the body. Continuously replacing the single pre-shaped access catheter in hopes of obtaining the proper curvature would be expensive and time consuming, possibly placing the patient at additional risk.

Further, some steerable guide catheters and delivery catheters have been developed to more effectively navigate through the tortuous pathways of some body lumens, particularly the vascular system. However, navigation through such lumens typically only requires steering the catheter tip toward a particular branch at a bifurcation, a relatively simple maneuver. Such steerability, basically the ability to form a single curvature, is generally inadequate for accessing and directing the catheter toward a target in a cavity. In particular, when targeting the mitral valve within the cavity of the left atrium or left ventricle, many more variables are present, such as the type of approach, the variability of anatomy and the various targets associated with the mitral valve, such as various points on the leaflets, the commissures, the free edges, the chordae tendinae, etc. These variables increase the need for a steerable guide catheter that can provide a higher degree of articulation than a single curve catheter or a catheter which does not provide compound curves in an adjustable manner.

Additionally, some guiding catheters have steering mechanisms that operate using pullwires. Such pullwires are typically attached to the distal end of a catheter and, when placed under tension, operate to steer the catheter. However, the attachment of pullwires may fail when the pullwire is subjected to the forces required to steer or guide the catheter through the desired range of angles and curves. Pullwires may be soldered or welded in place, thereby strengthening the connection to the catheter, but this adds to manufacturing time and costs, and may introduce hazardous chemicals necessitating additional cleanup and processing before the device can be suitably and safely introduced into the body. Further still, a soldered or welded connection may result in a fairly rigid connection between the pullwire and the distal end of the catheter which may fail or break when placed under stress.

Furthermore, when multi-catheter systems are used, such as when one catheter is nested within another, maintaining the rotational relationship between the catheters requires additional mechanisms to prevent or limit the unwanted rotation of one catheter relative to another. Such multi-catheter systems can include a keyway component and a corresponding key. In order to provide the desired functionality, the key component must have sufficient mechanical hardness, and for this reason such catheters typically employ keys made from metal, such as stainless steel. However, the use of stainless steel or other metal necessitates machining of the component, and expensive process adding to the manufacturing cost of the resulting device. Additionally, adhesives are required in order to attach the stainless steel keys to a plastic catheter. The adhesive bond between the machined, stainless steel key and the plastic catheter may fail, resulting in loss of the intended keying function. Furthermore, the use of adhesives involves the use of additional chemicals and curing reaction products, and may require the expenditure of additional time and effort to prepare the catheter for safe introduction into the body.

For these reasons, it would be desirable to provide a guiding catheter system which is capable of being positioned within a target body cavity in a desired orientation. The system should have a steering mechanism capable of handling the forces required to curve and steer the catheter system in the desired position and through the desired range of angles necessary to achieve a desired orientation. Furthermore, the system should have a feature for preventing the unwanted rotation of one component relative to another, and these features should be capable of operating safely and effectively in a physiological environment. In addition, these features should be provided at low manufacturing time and cost. At least some of the embodiments disclosed below are directed toward these objectives.

BRIEF SUMMARY

Certain embodiments of the present disclosure include a guidance system for accessing a target area (e.g., mitral valve, tricuspid valve, other heart valve, or other heart tissue) within a body, the guidance system including a guidable catheter having a proximal end and a distal end, with a tip ring attached to the distal end. The tip ring has one or more saddles configured such that a pullwire passing through a pullwire channel in the tip ring can be looped over the saddle and back down through the pullwire channel or through another pullwire channel. When tension is applied to the pullwire, the pullwire engages against the saddle and thereby subjects the guidable catheter to a curving or steering force. The use of a saddle eliminates the need for a soldered or welded connection at the distal end of the catheter and is designed to reduce and/or spread the stresses placed on the pullwires at the distal connection over a larger surface area.

Certain embodiments include a tip ring having one or more indentations extending proximally from a distal edge of the tip ring, with a saddle being disposed within the indentation as a raised surface within the indentation. Certain embodiments include one or more saddles having a curved surface advantageous in preventing, reducing, and/or eliminating the formation of stress risers in a pullwire engaged against the saddle.

Certain embodiments include a tip ring having three saddles, with the saddles circumferentially arranged and spaced at substantially 90 degrees apart from at least one other saddle (e.g., about 90 degrees, about 90 degrees, and about 180 degrees).

Certain embodiments include additional catheters coaxially positioned within or without the steerable guide catheter. In certain embodiments, an inner catheter is positioned at least partially within a lumen of the guide catheter and is axially translatable within the guide catheter. In certain embodiments, a multi-catheter system includes a keying feature configured to prevent rotation of the inner catheter relative to the outer catheter, the keying feature including a key joined to the inner catheter or outer catheter and a corresponding keyway disposed opposite the key and configured to receive the key, the key being formed at least partially from a chemically compatible plastic and being chemically bonded to the inner catheter or outer catheter.

Certain embodiments include keys having a hygroscopicity such that moisture absorption of the key in physiological conditions is 1 percent or less by weight. Certain embodiments include keys formed from a polyamide (e.g., nylon-12), and certain embodiments include keys formed from a polyamide that includes a filler material of glass microstructures (e.g., glass fibers or microspheres). In certain embodiments, glass microspheres having a diameter of about 5 microns to about 15 microns, or about 8 microns to about 10 microns, are provided in the key in an amount of about 10 percent to about 40 percent by weight, or about 15 percent to about 35 percent by weight, or about 20 percent to about 30 percent by weight, or about 25 percent by weight.

Certain embodiments may be useful in a tissue fixation and/or tissue repair procedure. For example, certain embodiments can be used to access a target area in a mitral valve fixation and/or repair procedure. Additionally, or alternatively, certain embodiments may be used in a different heart tissue procedure, such as a tricuspid valve, pulmonary valve, or aortic valve fixation and/or repair procedure, for example.

Additional disclosure regarding fixation devices and catheter guiding systems may be found in U.S. Pat. No. 7,666,204, PCT Publication No. WO 2004/103162, and U.S. patent application Ser. No. 14/216,787, the disclosures of each of which are incorporated herein in their entirety.

Other aspects and advantages of the invention will be apparent from the following description and the appended claims. The various characteristics described above, as well as other features, will be readily apparent to those skilled in the art upon reading the following detailed description, and by referring to the accompanying drawings. This summary is therefore not intended to identify key or essential features of the claimed subject matter, nor is it intended to be used as an aid in limiting the scope of the claims.

BRIEF DESCRIPTION OF THE DRAWINGS

In order to describe various features and concepts of the present disclosure, a more particular description of certain subject matter will be rendered by reference to specific embodiments which are illustrated in the appended drawings. The embodiments contemplated herein may not be drawn to scale. Understanding that these drawings depict just some example embodiments and are not to be considered to be limiting in scope, various embodiments will be described and explained with additional specificity and detail through the use of the accompanying drawings in which:

FIGS. 5A-5I illustrate embodiments of catheters within a multi-catheter system;

DETAILED DESCRIPTION

I. Catheter Guiding System

Figure 1A:
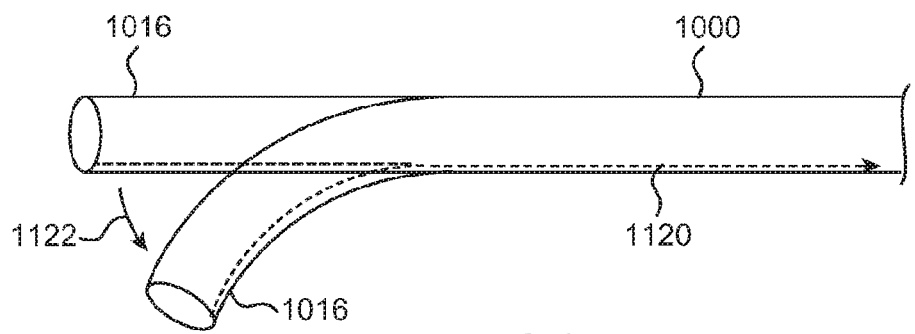
FIGS. 1A-1D illustrate embodiments of steerable guide catheters being curved using pullwires attached to distal ends of the catheters.

FIGS. 1A-1D illustrate embodiments of steerable guide catheters. To provide a higher degree of control and variety of possible curvatures, steering mechanisms may be used to create the curvatures and/or to position the catheters. In some embodiments, the steering mechanisms comprise cables or pullwires within the wall of the catheter. As shown in FIG. 1A, the guide catheter 1000 may include a pullwire 1120 slidably disposed in lumens within the wall of the catheter 1000 extending to the distal end 1016. By applying tension to the pullwire 1120 in the proximal direction, the distal end 1016 curves in the direction of the pullwire 1120 as illustrated by arrow 1122.

Figure 1B:
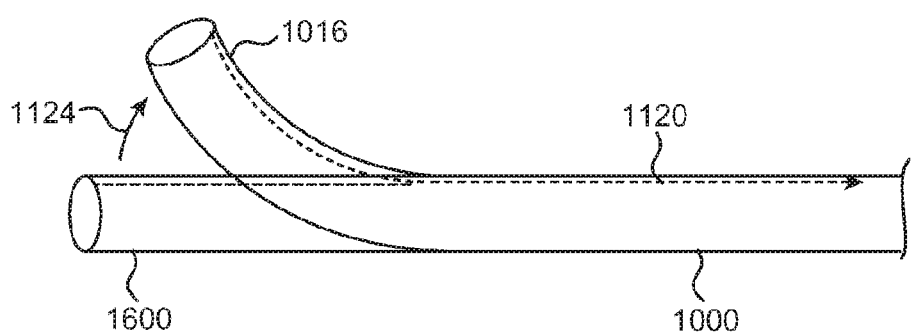
Figure 1C:
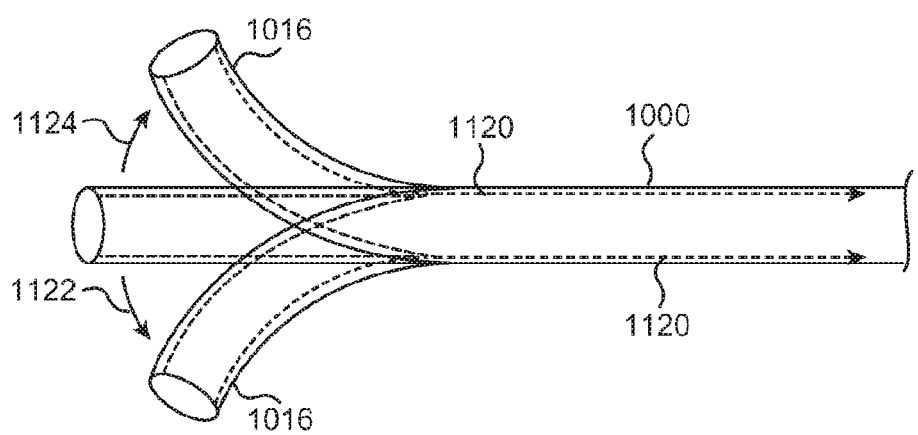

Likewise, as shown in FIG. 1B, placement of the pullwire 1120 along the opposite side of the catheter 1000 will allow the distal end 1016 to curve in the opposite direction, as illustrated by arrow 1124, when tension is applied to the pullwire 1120. Thus, referring to FIG. 1C, diametrically opposing placement of pullwires 1120 within the walls of the catheter 1000 allows the distal end 1016 to be steered in opposite directions. This provides a means of correcting or adjusting a curvature. For example, if tension is applied to one pullwire to create a curvature, the curvature may be lessened by applying tension to the diametrically opposite pullwire.

Figure 1D:
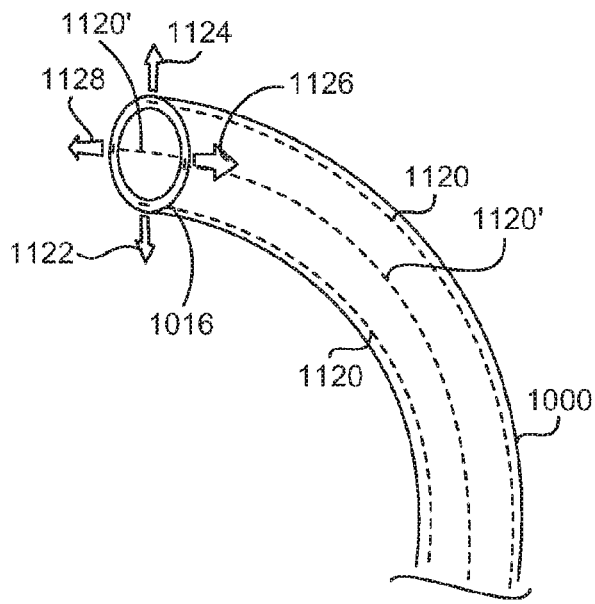

Referring now to FIG. 1D, an additional set of opposing pullwires 1120' may extend within the wall of the catheter 1000 as shown. This combination of pullwires 1120, 1120' allows curvature of the distal end in at least four directions illustrated by arrows 1122, 1124, 1126, 1128. In this example, pullwires 1120 create the primary curve 1100 of the outer guide catheter 1000 and the pullwires 1120' create the lift. It may be appreciated that FIGS. 13A-13D also pertain to the inner guide catheter 1020. For example, in FIG. 1D, pullwires 1120 may create the secondary curve 1104 of the inner guide catheter 1020 and the pullwires 1120' create the angle theta 1070.

Such pullwires 1120 and/or pullwires 1120' and associated lumens may be placed in any arrangement, singly or in pairs, symmetrically or nonsymmetrically and any number of pullwires may be present. This may allow curvature in any direction and about various axes. For example, in some embodiments, a steerable guide catheter may include three pullwires arranged about the wall of the catheter (e.g., arranged symmetrically at about 120 degrees apart, arranged at about 90, 90, and 180 degrees apart, etc.).

Figure 2:
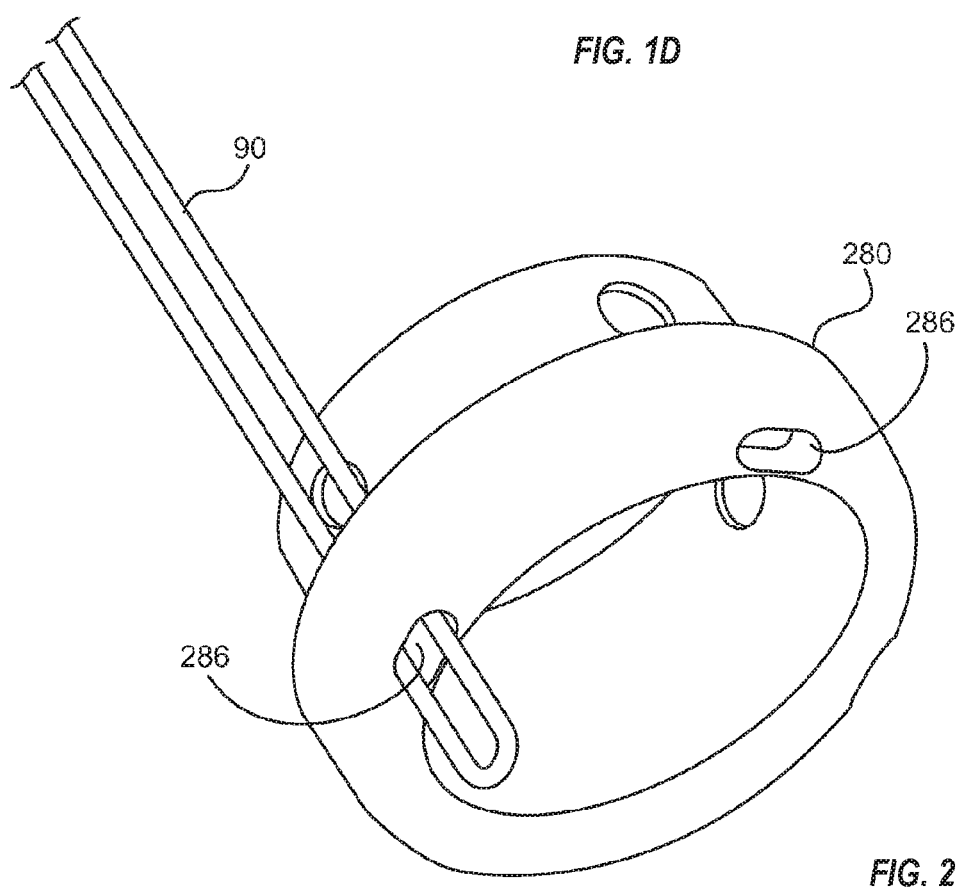
FIG. 2 is an embodiment of a tip ring attachable to the distal end of a steerable guide catheter.

The pullwires 1120, 1120' may be fixed at any location along the length of the catheter by any suitable method, such as gluing, tying, soldering, or potting, to name a few. When tension is applied to the pullwire, the curvature forms from the point of attachment of the pullwire toward the proximal direction. Therefore, curvatures may be formed throughout the length of the catheter depending upon the locations of the points of attachment of the pullwires. Typically, however, the pullwires will be attached near the distal end of the catheter, optionally to an embedded tip ring 280, illustrated in FIG. 2. As shown, the pullwire 1120 passes through an orifice 286 in the tip ring 280, forms a loop shape and then passes back through the orifice 286 and travels back up through the catheter wall (not shown). In addition, the lumens which house the pullwires may be straight, as shown in FIGS. 1A-1D, or may be curved.

Figure 3A:
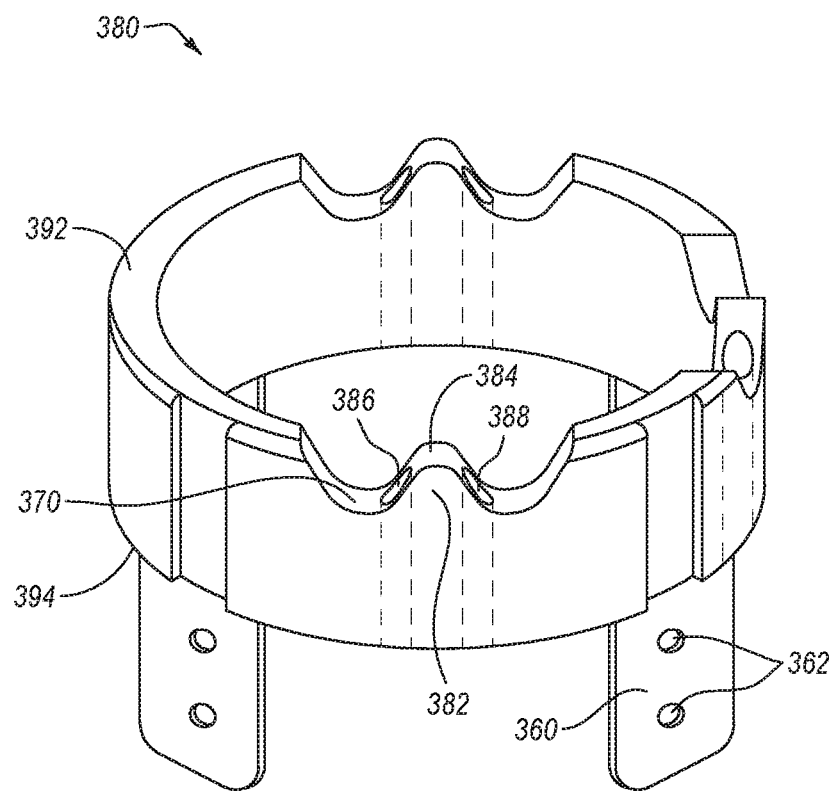
FIGS. 3A-3C is another embodiment of a tip ring attachable to the distal end of a steerable guide catheter and including a saddle configured to allow a pullwire to engage against when subjected to tension.

In some embodiments, such as the embodiment illustrated in FIG. 3A, a steerable guide catheter can include a tip ring 380 having one or more saddles 382. In this embodiment, the tip ring 380 includes a saddle 382 disposed between a first pullwire channel 386 and a second pullwire channel 388. The saddle 382 and first and second pullwire channels 386 and 388 are configured such that a pullwire positioned through the first and second pullwire channels 386 and 388 can engage, abut, and/or rest against the saddle 382.

Figure 3B:
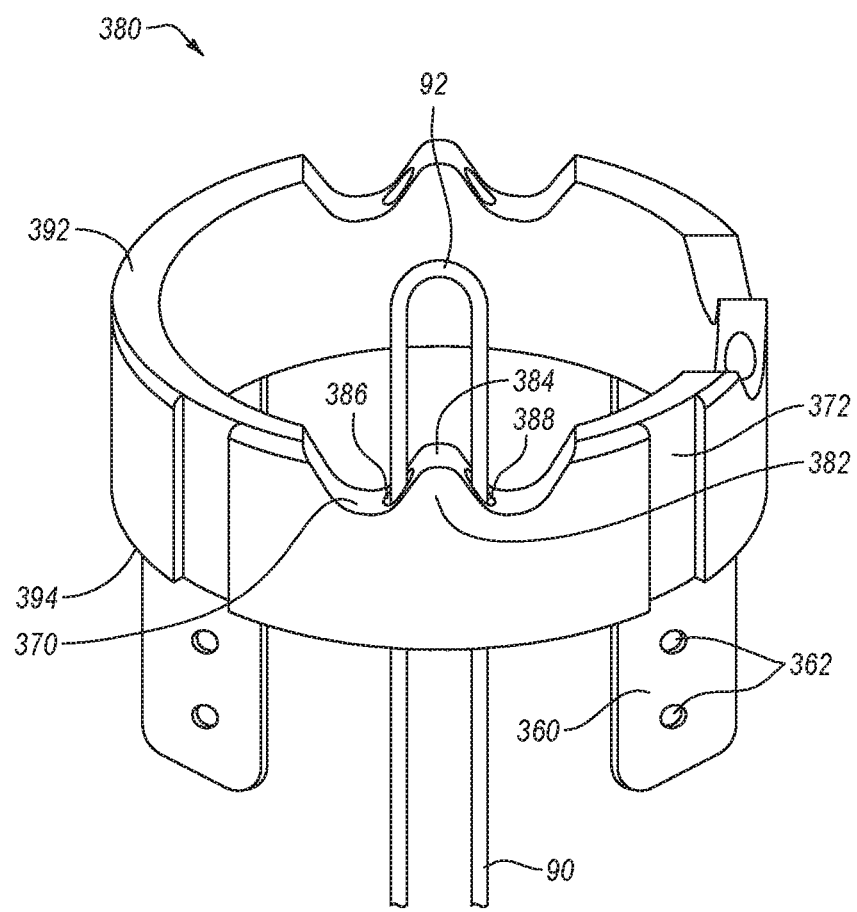
Figure 3C:
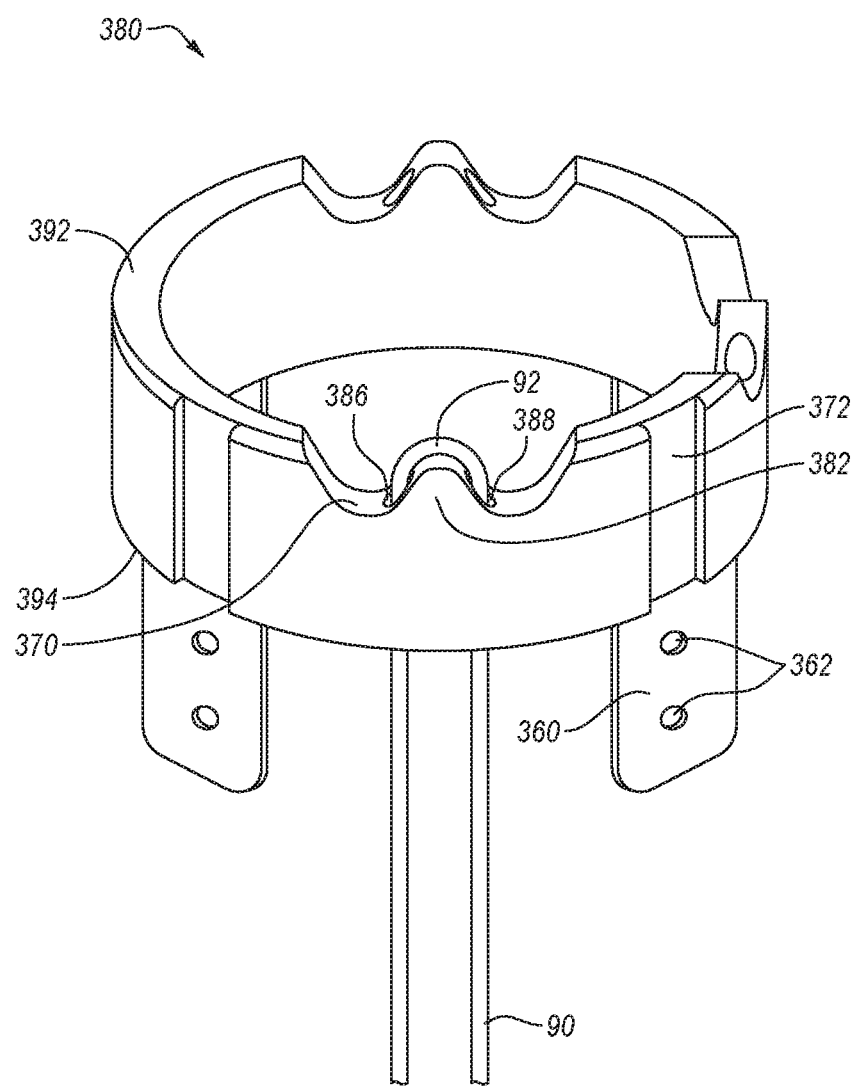

For example, as illustrated in FIG. 3B, a pullwire 90 may be associated or connected to the tip ring 380 by passing through the first pullwire channel 386 before looping around to pass back through the second pullwire channel 388 and to form a looped portion 92. As illustrated in FIG. 3C, when the pullwire 90 is subjected to tension or otherwise pulled taught, the looped portion 92 is brought against the saddle 382, causing the pullwire 90 to abut, engage with, or rest against the saddle 382 of the tip ring 380. A tip ring 380 formed in this manner provides many advantages, particularly as compared to a tip ring that must be joined to a pullwire via adhesives, welding and the like. For example, when a pullwire 90 is placed under tension, the forces are distributed over a large portion of the tip ring 380 rather than on a weld or adhesive joint, thereby reducing the risk of pullwire detachment, device failure, and concomitant risk to the patient. In addition, the saddle 382 is capable of positioning the pullwire 90 in a configuration that avoids the formation of stress risers or stress points within the pullwire 90, particularly as compared to tip rings requiring tight bends or curves over corners or hard edges.

The illustrated embodiment of the tip ring 380 also includes a distal edge 392 and a proximal edge 394, with an indentation 370 extending proximally from the distal edge 392 of the tip ring 380, with the saddle 382 being disposed within the indentation 370 of the tip ring 380. In the illustrated embodiment, the saddle 382 is formed as a raised portion or surface disposed within the indentation 370 and extending distally from the indentation 370. Other embodiments may omit indentations, or may include one or more indentations of alternative size and/or shape. For example, some embodiments may include pullwire channels that extend from the proximal edge completely through to the distal edge of the tip ring. In such embodiments, the saddle is disposed between the first and second pullwire channels, and may be formed as a raised surface extending from the distal edge of the tip ring (e.g., extending further distally).

Other embodiments may include one or more indentations of alternative size and/or shape. For example, an indentation may be configured to be substantially semicircular in shape. Alternatively, an indentation may be configured with a combination of different curvature radii. In addition, an indentation may include corners and/or may be formed with a rectangular or other polygonal shape or feature.

The tip ring 380 of FIGS. 3A-3C includes a first pullwire channel 386 and a second pullwire channel 388 that each extend from the proximal edge 394 through to the indentation 370, thereby allowing the saddle 382 to be exposed as part of the outer distal surface of the tip ring 380, and also allowing the looped portion 92 of the pullwire 90 to be exposed when positioned against the saddle 382. In other embodiments, the pullwire channels do not pass completely through to a distal edge, indentation, or other distal surface of the tip ring. For example, a contiguous pullwire channel may pass from a proximal edge partly towards a distal surface before cornering, turning, or otherwise turning and passing back toward the proximal edge, thereby forming an internal channel within the tip ring. In such embodiments, the saddle is defined by the distal-most apex of the curve in the pullwire channel. When a pullwire is threaded or passed through the pullwire channel, the looped portion of the pullwire positioned within curve of the pullwire channel will engage against the saddle when the pullwire is subjected to tension.

In other embodiments, a tip ring may include a channel that extends radially through all or a portion of the peripheral wall of the tip ring (instead of axially), such as a channel formed through a hanging lip, cutout, or similar structure extending proximally off of the proximal edge of the tip ring. In such embodiments, the saddle is defined as the portion of the lip, cutout, or other structure proximal to the channel, such that when a pullwire is threaded or passed through the pullwire channel and placed under tension, the looped portion of the pullwire engages against the portion of the portion of the lip, cutout, or other structure proximal to the channel.

As shown in FIGS. 3A-3C, the saddle 382 is formed as a raised portion or raised surface within the indentation 370 of the tip ring 380. The raised surface of the saddle 382 has a curved shape with an apex 384 disposed between the first pullwire channel 386 and the second pullwire channel 388, and the apex 384 does not extend distally to the same distal extension of the distal edge 392 of the tip ring 380. In other embodiments, the saddle 382 may be formed with alternative sizes and shapes. For example, some embodiments may include a saddle formed as a raised surface that extends to the distal edge or extends beyond the distal edge of the tip ring. In preferred embodiments, such as the illustrated embodiment, the axial distance between the distal extension of the distal edge 392 and the apex 384 of the saddle 382 is substantially equal to or greater than the diameter of the pullwire 90. In this manner, pullwire 90 does not extend farther distally than the distal edge 392 when engaged against the saddle 382 (see, e.g., FIG. 3C).

In the embodiment of FIGS. 3A-3C, the raised area or surface forming the saddle 382 is generally symmetrically disposed between the first and second pullwire channels 386 and 388 and the saddle 382 is substantially symmetric in shape such that the apex 384 of the saddle 382 is substantially equidistant from the first and second pullwire channels 386 and 388. In one embodiment, the shape of the surface forming the saddle 382 is semi-circular in shape and forms a smooth, substantially circular bearing surface over which the stresses placed on the pullwires when placed under tension are spread over a larger, substantially smooth surface area. In other embodiments, the relative positions of the saddle 382 and the first and second pullwire channels 386 and 388 may be alternately configured. For example, in some embodiments, the saddle is not disposed symmetrically between the pullwire channels and/or the apex of the saddle is not symmetrically shaped or equidistantly positioned between the pullwire channels and/or the saddle is not symmetrically shaped.

In the embodiment of FIGS. 3A-3C, the raised area or surface forming the saddle 382 circumferentially extends beyond the first pullwire channel 386 and beyond the second pullwire channel 388. In other embodiments, the raised portion or surface forming the saddle is narrower relative to the pullwire channels, such that the raised area does not circumferentially extend beyond the first pullwire channel and/or the second pullwire channel.

The embodiment of FIGS. 3A-3C includes three indentations 370 and three saddles 382. In this embodiment, each indentation 370 includes one of the saddles 382, and each indentation 370 is arranged to be circumferentially spaced apart at about 90 degrees from another indentation (e.g., total spacing of about 90 degrees, about 90 degrees, and about 180 degrees). Any other arrangement of indentations and saddles may also be used. For example, some embodiments may include one or two saddles, or may include more than three (e.g., four, five, six, or more), and these saddles may be arranged in an equidistant or non-equidistant fashion.

The illustrated tip ring 380 also includes a skirt 360 joined to the proximal edge 394 and extending proximally from the proximal edge 394. In this embodiment, the skirt is slotted at areas correlating with the pullwire 90 or correlating with areas where a pullwire may be positioned in order to provide space for the pullwire 90. In other embodiments, a skirt may include a full contiguous circumference. The skirt 360 can function to aid in positioning and joining the tip ring to the distal end of a steerable guide catheter. In addition, the skirt 360 can include one or more holes 362 to aid in the flow and transport of an adhesive and/or polymer coating added to the tip ring 380 and steerable guide catheter. The tip ring can also include one or more keyways 372 (and/or notches, channels, grooves, or other similar structures) also configured to receive an adhesive and/or polymer for attaching the tip ring 380 to a catheter or strengthening the attachment to a catheter. The polymer coating can be formed, for example, of a polyether block amide (e.g., Pebax®), polyester, nylon, or other polymer suitable for forming a cover over the tip ring 380 and the distal end of a catheter.

The preferred dimensions of the pullwires, the pullwire channels, and/or the saddles will vary depending on the particular application, machining tolerances, and other factors. The following exemplary dimensions are provided by way of example only, and are directed to the mitral valve application disclosed in Section IV below. For example, the radius of a saddle and the diameter of the pullwires may be configured so as to provide a relatively gradual bend in a given pullwire as it is positioned over a saddle, thereby avoiding any kinking or the creation of stress risers in the pullwire due to an overly abrupt bend. In one example, the diameter of the pullwires can range from about 0.0050 inches to about 0.0150 inches (e.g., about 0.0105 inches), and the saddles of the tip ring are configured with a generally semi-circular shape having a radius that ranges from about 0.0025 inches to about 0.0075 inches (e.g., about 0.0050 inches to about 0.0055 inches). In such embodiments, the ratio of the pullwire diameter to the saddle radius is about 2:1. In other embodiments, the ratio of the pullwire diameter to the saddle radius can be about 3:1 or about 4:1 or higher; however, in preferred embodiments the ratio is not so high as to create a kink or stress point within the pullwire. In other embodiments, the ratio of the pullwire diameter to the saddle radius can be about 1:1, or about 1:1.5, or about 1:2, or about 1:2.5, or about 1:3.

II. Multi-Catheter Embodiments

Some embodiments of catheter guiding systems include more than one steerable guide catheter or include a steerable guide catheter used or associated with one or more other catheters. For example, in some embodiments, a steerable guide catheter may include a tip ring and one or more pullwires, and the steerable guide catheter may be associated with (e.g., nested within or encircling) one or more additional catheters. Curvatures may be formed in the catheters of a multi-catheter system by precurving, steering or any suitable means. Precurving involves setting a specific curvature in the catheter prior to usage, such as by heat setting a polymer or by utilizing a shape-memory alloy. Since the catheters are generally flexible, loading of the catheter on a guidewire, dilator obturator or other introductory device straightens the catheter throughout the curved region. Once the catheter is positioned in the anatomy, the introductory device is removed and the catheter is allowed to relax back into the precured setting.

Figure 4:
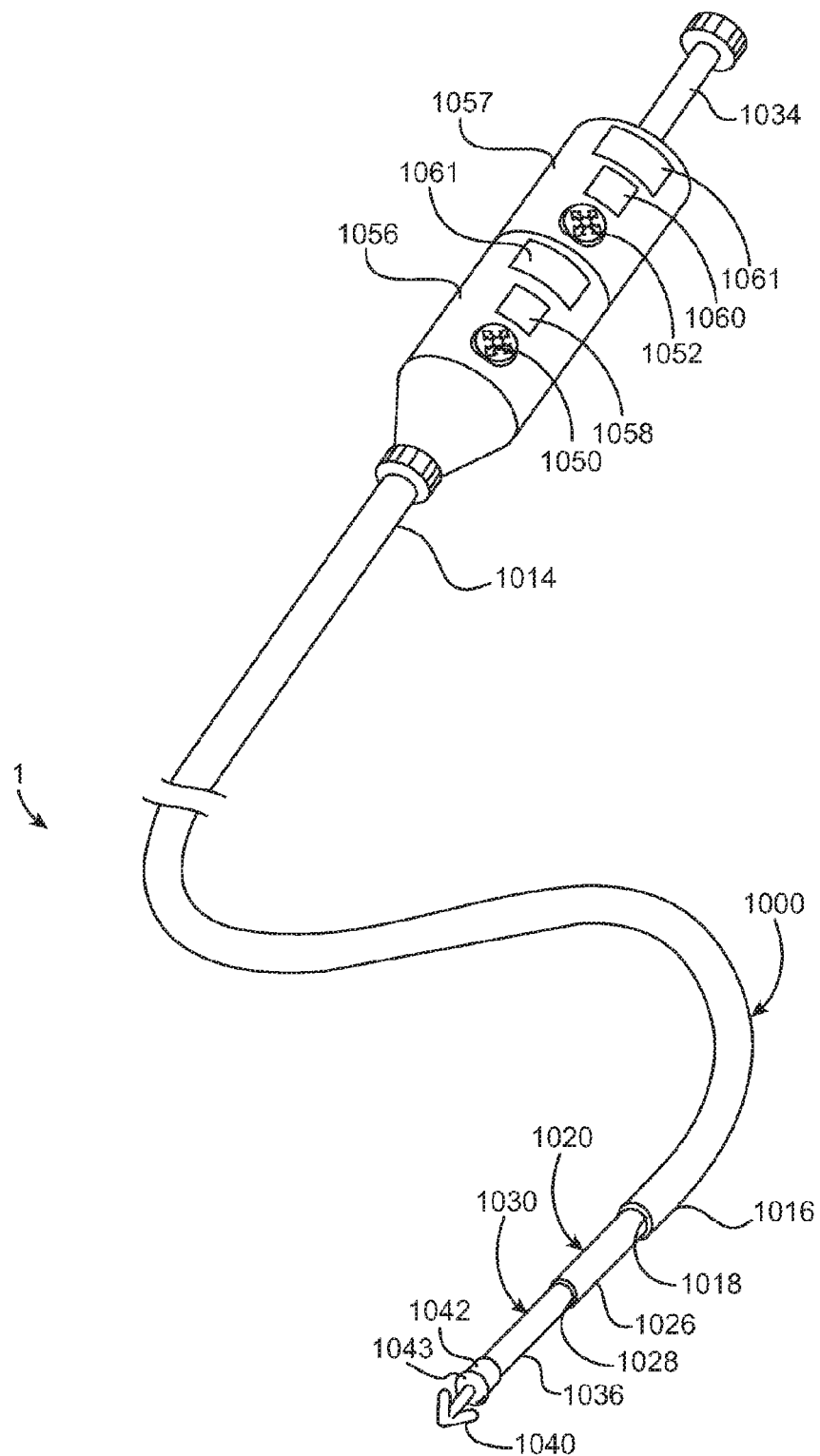
FIG. 4 is an embodiment of a multi-catheter guiding system.

Referring to FIG. 4, an embodiment of a multi-catheter guiding system 1 of the present invention is illustrated. The system 1 comprises an outer guide catheter 1000, having a proximal end 1014, a distal end 1016, and a central lumen 1018 therethrough, and an inner guide catheter 1020, having a proximal end 1024, distal end 1026 and central lumen 1028 therethrough, wherein the inner guide catheter 1020 is positioned coaxially within the central lumen 1018 of the outer guide catheter 1000, as shown. The distal ends 1016, 1026 of catheters 1000, 1020, respectively, are sized to be passable to a body cavity, typically through a body lumen such as a vascular lumen. Thus, the distal end 1016 preferably has an outer diameter in the range of approximately 0.040 in. to 0.500 in., more preferably in the range of 0.130 in. to 0.320 in. The central lumen 1018 is sized for the passage of the inner guide catheter 1020; the distal end 1026 preferably has an outer diameter in the range of approximately 0.035 in. to 0.280 in., more preferably 0.120 in to 0.200 in. The central lumen 1028 is sized for the passage of a variety of devices therethrough. Therefore, the central lumen 1028 preferably has an inner diameter in the range of approximately 0.026 in. to 0.450 in., more preferably in the range of 0.100 in. to 0.180 in.

FIG. 4 illustrates an interventional catheter 1030 positioned within the inner guide catheter 1020 which may optionally be included in system 1, however other interventional devices may be used. The interventional catheter 1030 has a proximal end 1034 and a distal end 1036, wherein an interventional tool 1040 is positioned at the distal end 1036. In this embodiment, the interventional tool 1040 comprises a detachable fixation device or clip. Optionally, the interventional catheter 1030 may also include a nosepiece 1042 having a stop 1043, as shown. The stop 1043 prevents the interventional tool 1040 from entering the central lumen 1028 of the inner guide catheter 1020. Thus, the interventional catheter 1030 may be advanced and retracted until the stop 1043 contacts the distal end 1026 of the inner guiding catheter 1020 preventing further retraction. This may provide certain advantages during some procedures. It may be appreciated that in embodiments which include such a stop 1043, the interventional catheter 1030 would be pre-loaded within the inner guide catheter 1020 for advancement through the outer guiding catheter 1000 or both the interventional catheter 1030 and the inner guiding catheter 1020 would be pre-loaded into the outer guiding catheter 1000 for advancement to the target tissue. This is because the stop 1043 prevents advancement of the interventional catheter 1030 through the inner guiding catheter 1020.

The outer guide catheter 1000 and/or the inner guide catheter 1020 can be precurved and/or have steering mechanisms to position the distal ends 1016, 1026 in desired directions. Precurvature or steering of the outer guide catheter 1000 can direct the distal end 1016 in a first direction to create a primary curve while precurvature and/or steering of the inner guide catheter 1020 can direct distal end 1026 in a second direction, differing from the first, to create a secondary curve. Together, the primary and secondary curves can form a compound curve. Advancement of the interventional catheter 1030 through the coaxial guide catheters 1000, 1020 guides the interventional catheter 1030 through the compound curve toward a desired direction, usually in a direction which will allow the interventional a catheter 1030 to reach its target.

Steering of the outer guide catheter 1000 and/or inner guide catheter 1020 may be achieved by actuation of one or more steering mechanisms. Actuation of the steering mechanisms is achieved with the use of actuators which are typically located on handles connected with each of the catheters 1000, 1020. As illustrated in FIG. 4, handle 1056 is connected to the proximal end 1014 of the outer guide catheter 1000 and remains outside of the patient's body during use. Handle 1056 includes steering actuator 1050 which may be used to bend, arc or reshape the outer guide catheter 1000, such as to form a primary curve. Handle 1057 is connected to the proximal end (not shown) of the inner guide catheter 1020 and may optionally join with handle 1056 to form one larger handle, as shown. Handle 1057 includes steering actuator 1052 which may be used to bend, arc or reshape the inner guide catheter 1020, such as to form a secondary curve and move the distal end 1026 of the inner guide catheter 1020 through an angle. In addition, locking actuators 1058, 1060 may be used to actuate locking mechanisms to lock the catheters 1000, 1020 in a particular position.

The outer guide catheter 1000 and inner guide catheter 1020 may have the same or different construction which may include any suitable material or combination of materials to create the above described curvatures. For clarity, the examples provided will be in reference to the outer guide catheter 1000, however it may be appreciated that such examples may also apply to the inner guide catheter 1020.

In embodiments in which the catheter is steerable, the catheter 1000 may be comprised of one or more of a variety of materials, either along the length of the catheter 1000 or in various segments. Example materials include polyurethane, Pebax, nylon, polyester, polyethylene, polyimide, polyethylenetelephthalate (PET), polyetheretherketone (PEEK). In addition, the walls of the catheter 1000 may be reinforced with a variety of structures, such as metal braids or coils. Such reinforcements may be along the length of the catheter 1000 or in various segments.

For example, referring to FIG. 5A, the catheter 1000 may have a proximal braided segment 1150, a coiled segment 1152 and distal braided segment 1154. The proximal braided segment 1150 provides increased column strength and torque transmission. The coiled segment 1152 provides increased steerability. The distal braided segment 1154 provides a blend of steerability and torque/column strength. In another example, referring to FIG. 5B, the outer guiding catheter 1000 has a proximal double-layer braided segment 1151 and a distal braided segment 1154. Thus, the proximal double-layer segment 1151 comprises a multi-lumen tube 1160 (having steering lumens 1162 for pullwires, distal ends of the steering lumens 1162 optionally embedded with stainless steel coils for reinforcement, and a central lumen 1163), an inner braided layer 1164, and an outer braided layer 1166, as illustrated in the cross-sectional view of FIG. 5C. Similarly, FIG. 5D provides a cross-sectional view of the distal braided segment 1154 comprising the multi-lumen tube 1160 and a single braided layer 1168. In a further example, referring to FIG. 5E, the inner guiding catheter 1020 comprises a multi-lumen tube 1160 without reinforcement at its proximal end, a single braided layer middle segment 1170 and a single braided layer distal segment 1171. Each of the single braided layer segments 1170, 1171 have a multi-lumen tube 1160 and a single layer of braiding 1168, as illustrated in cross-sectional view FIG. 5F. However, the segments 1170, 1171 are comprised of polymers of differing durometers, typically decreasing toward the distal end.

Figure 5G:
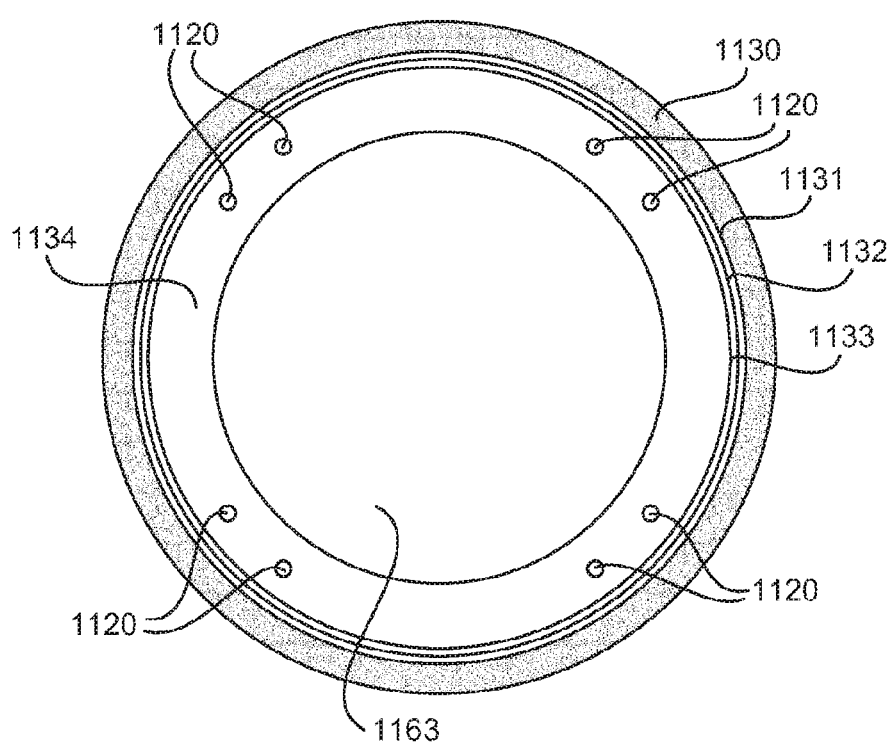

FIG. 5G illustrates another example of a cross-section of a distal section of an outer guiding catheter 1000. Here, layer 1130 comprises 55 D Pebax and has a thickness of approximately 0.0125 in. Layer 1131 comprises a 30 ppi braid and has a thickness of approximately 0.002 in. by 0.0065 in. Layer 1132 comprises 55 D Pebax and has a thickness of approximately 0.006 in. Layer 1133 comprises 30 ppi braid and has a thickness of approximately 0.002 in by 0.0065 in. And finally, layer 1134 comprises Nylon 11 and includes steering lumens for approximately 0.0105 in. diameter pullwires 1120. Central lumen 1163 is of sufficient size for passage of devices.

Figure 5H:
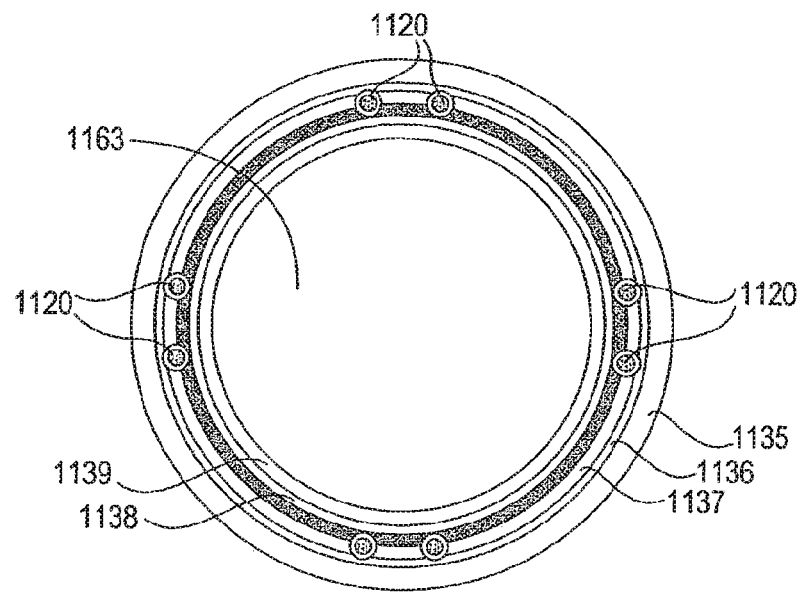
Figure 5I:
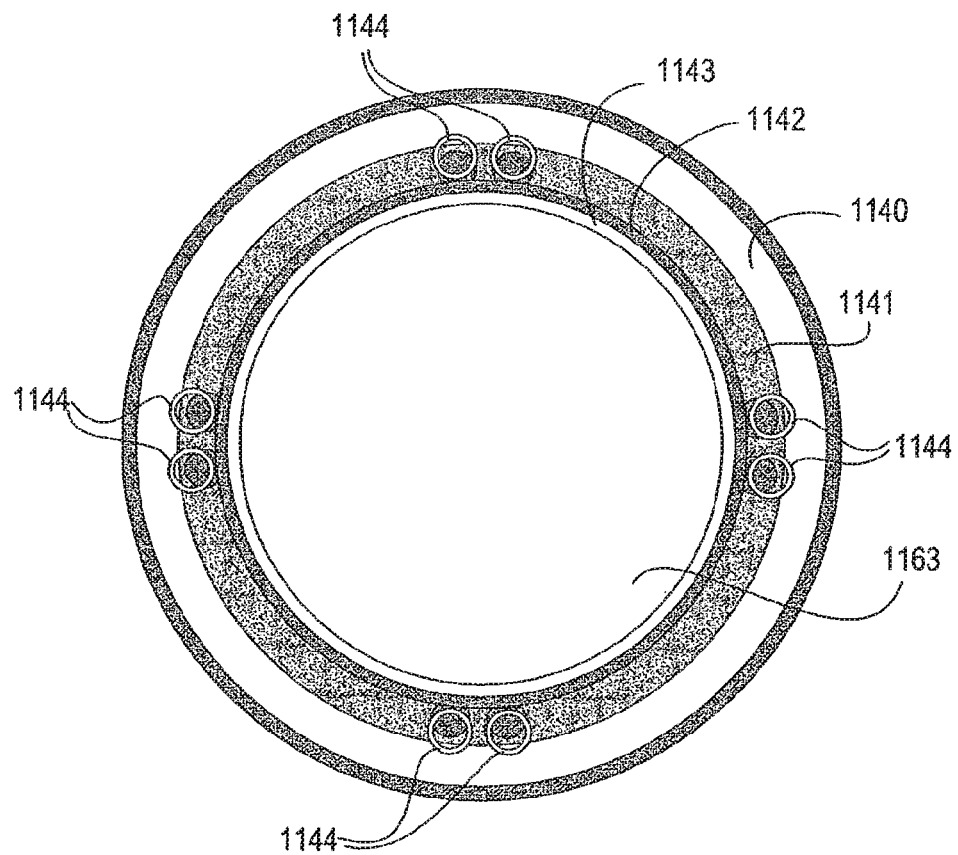

FIGS. 5H-5I illustrate additional examples of cross-sections of an inner guiding catheter 1020, FIG. 5H illustrating a cross-section of a portion of the distal end and FIG. 5I illustrating a cross-section of a more distal portion of the distal end. Referring to FIG. 5H, layer 1135 comprises 40 D polymer and has a thickness of approximately 0.0125 in. Layer 1136 comprises a 30 ppi braid and has a thickness of approximately 0.002 in. by 0.0065 in. Layer 1137 comprises 40 D polymer and has a thickness of approximately 0.006 in. Layer 1138 comprises a 40 D polymer layer and has a thickness of approximately 0.0035 in. And finally, layer 1139 comprises a 55 D liner. In addition, coiled steering lumens are included for approximately 0.0105 in. diameter pullwires 1120. And, central lumen 1163 is of sufficient size for passage of devices. Referring to FIG. 5I, layer 1140 comprises a 40 D polymer, layer 1141 comprises a 35 D polymer, layer 1142 comprises a braid and layer 1143 comprises a liner. In addition, coiled steering lumens 1144 are included for pullwires and central lumen 1163 is of sufficient size for passage of devices.

III. Keying Feature

Figure 6A:
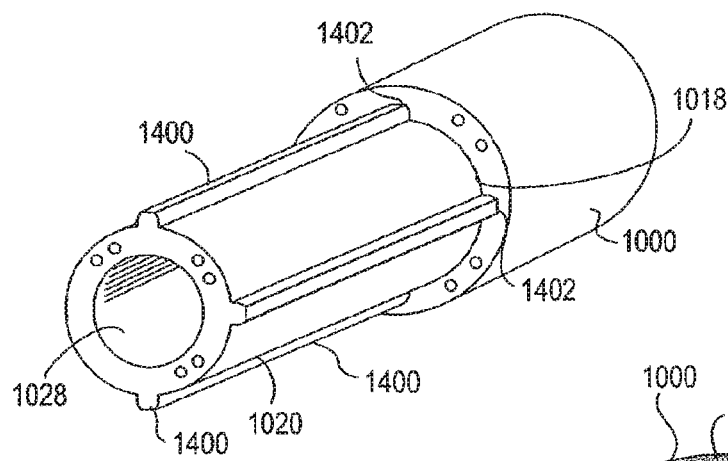
FIGS. 6A-6C illustrate a keying feature of a multi-catheter system.
Figure 6B:
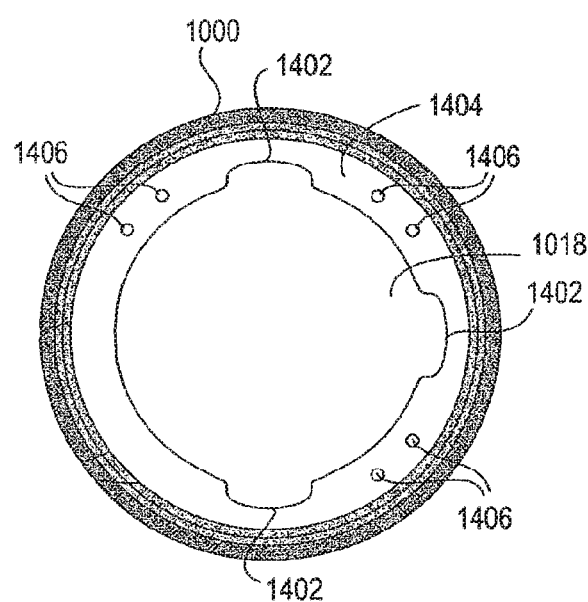
Figure 6C:
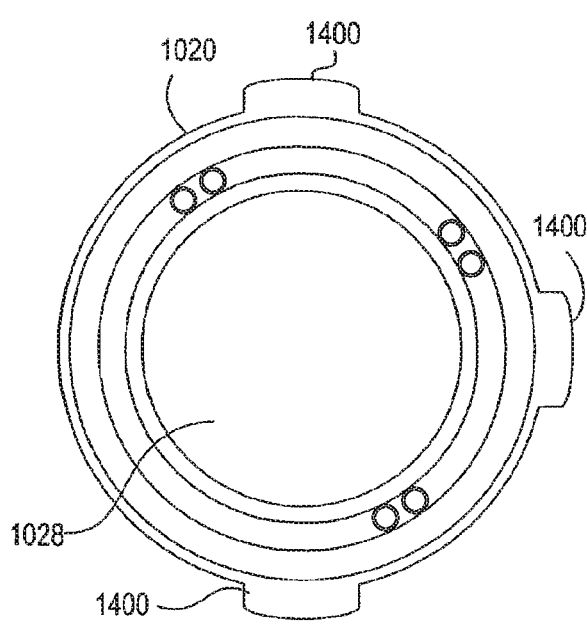

FIGS. 6A-6C illustrate an embodiment of a keying feature which may be incorporated into the catheter shafts. The keying feature is used to maintain the rotational relationship between the inner and outer guide catheters in order to assist in steering capabilities. As shown in FIG. 6A, the inner guide catheter 1020 may include one or more keys 1400 which extend radially outwardly. In this example, three keys 1400 are present. Such an embodiment can provide certain advantages. For example, when three keys are spaced apart in a non-equidistant radial fashion (e.g., about 90 degrees, about 90 degrees, and about 180 degrees), placement of the inner catheter 1020 relative to the outer catheter 1000 is restricted to one orientation. This can reduce user error in placement and positioning of the catheters relative to each other, as only the correct orientation is allowed.

Likewise, the outer guide catheter 1000 includes corresponding keyways 1402 which align with the keys 1400. Thus, in this example, the catheter 1000 includes three notches. In this manner, the inner guide catheter 1020 is able to be translated within the outer guide catheter 1000, however rotation of the inner guide catheter 1020 within the outer guide catheter 1000 is prevented by the keying feature; specifically, the interlocking keys 1400 and keyways 1402. Such keying helps maintain a known correlation of position between the inner guide catheter 1020 and outer guide catheter 1000. Since it may be desired for the inner and outer guide catheters 1020, 1000 to form curvatures in different directions, such keying ensures that the compound curvature formed by the separate curvatures in the inner and outer guide catheters 1020, 1000 is the compound curvature that is anticipated. Keying may also increase stability wherein the curvatures remain in position reducing the possibility of compensating for each other.

FIG. 6B illustrates a cross-sectional view of the outer guiding catheter 1000 of FIG. 6A. Here, the catheter 1000 includes a notched layer 1404 along the inner surface of central lumen 1018. The notched layer 1404 includes keyways 1402 in any size, shape, arrangement and number. Optionally, the notched layer 1404 may include lumens 1406, typically for passage of pullwires 1120. However, the lumens 1406 may alternatively or in addition be used for other uses. It may also be appreciated that the notched layer 1404 may be incorporated into the wall of the catheter 1000, such as by extrusion, or may be a separate layer positioned within the catheter 1000. Further, it may be appreciated that the notched layer 1404 may extend the entire length of the catheter 1000 or one or more portions of the length of the catheter 1000, including simply a small strip at a designated location along the length of the catheter 1000.

FIG. 6C illustrates a cross-sectional view of the inner guiding catheter 1020 of FIG. 6A. Here, the catheter 1020 includes keys 1400 along the outer surface of the catheter 1020. The keys 1400 may be of any size, shape, arrangement and number. It may be appreciated that the keys 1400 may be incorporated into the wall of the catheter 1020, such as by extrusion, may be included in a separate cylindrical layer on the outer surface of the catheter 1020, or the keys 1400 may be individually adhered to the outer surface of the catheter 1020. Further, it may be appreciated that the keys 1400 may extend the entire length of the catheter 1000 or one or more portions of the length of the catheter 1020, including simply a small strip at a designated location along the length of the catheter 1020.

Thus, the keying feature may be present along one or more specific portions of the catheters 1000, 1020 or may extend along the entire length of the catheters 1000, 1020. Likewise, the keyways 1402 may extend along the entire length of the outer guiding catheter 1020 while the keys 1400 extend along discrete portions of the inner guiding catheter 1000 and vice versa. It may further be appreciated that the keys 1400 may be present on the inner surface of the outer guiding catheter 1000 while the keyways 1402 are present along the outer surface of the inner guiding catheter 1020.

In preferred embodiments, the keys 1400 are formed of a plastic material that may be suitably used in an injection molding or similar manufacturing process not requiring any significant post-formation machining (e.g., as compared to a metal key formation process requiring several machining steps). In preferred embodiments, the plastic keys 1400 are chemically compatible with the catheter (e.g., inner guide catheter 1000) such that the keys 1400 are able to be thermally welded to the catheter so as to form a chemical bond with the catheter. This can provide the advantages of a strong, integrated bond and can avoid the necessity of adhesives, welding, and/or similar attachment means that introduce or risk introducing additional unwanted materials to the body and/or require additional cleaning procedures to prepare the catheter system for safe use in a patient.

In preferred embodiments, the plastic keys 1400 are formed of polyether, polyamide, or combinations such as polyether block amides (e.g., Pebax®). In more preferred embodiments, the plastic keys 1400 are formed from a polyamide, such as nylon, and the material is formed with a suitable hardness to provide the keying function of the multi-catheter system.

In some embodiments, the keys 1400 are formed from a nylon (e.g., nylon-12) combined with a filler material such as glass microstructures (e.g., glass microfibers and/or glass microspheres). Such embodiments can provide the advantages of suitable hardness without undue moisture absorption. In these and other embodiments, the key has a hygroscopicity such that moisture absorption in physiological conditions is 5 percent or less by weight or 2.5 percent or less by weight. In more preferred embodiments, the key has a hygroscopicity such that moisture absorption in physiological conditions is 1 percent or less by weight.

In preferred embodiments, the filler material includes glass microspheres included in the key in an amount of about 10 percent to about 40 percent by weight, or about 25 percent to about 35 percent by weight, or about 20 percent to about 30 percent by weight, or most preferably about 25 percent by weight. The glass microspheres can have a diameter within a range of about 5 microns to about 15 microns, or more preferably about 8 microns to about 10 microns. In other embodiments, glass microfibers may be used in place of or along with glass microspheres. Such glass microfibers are preferably sized so as to have the same functional size as the glass microspheres (e.g., a longest dimension within a range of about 5 microns to about 15 microns, or more preferably about 8 microns to about 10 microns).

In some embodiments, the use of glass microspheres or the use of a glass microsphere and glass fiber combination filler material can be advantageous as compared to a filler material of only glass fibers. For example, the use of glass microspheres as filler material has been unexpectedly shown to improve the flow and moldability of keys 1400 during formation and manufacturing steps. In addition, such embodiments are particularly advantageous for limiting the hygroscopicity of the keys 1400, as glass microspheres provide more volume for a given mass of material than other filler materials such as glass fibers.

Other components can also be added to the keys 1400. For example, the keys 1400 can include a nucleating agent to increase the crystalline content of the polymer structure forming the key. Suitable nucleating agents include derivatives of benzoic acid, such as sodium benzoate, kaolin, talc, and/or long-chain carboxylic acids (e.g., from about 10 to 30 carbon atoms, or from about 15 to 25 carbon atoms).

IV. Mitral Valve Repair

Embodiments of the catheter guiding system of the present disclosure may be used in a variety of applications for steering and guiding a catheter to a treatment site. In particular, embodiments of the catheter guiding system of the present disclosure may be used where a treatment site is accessed via the vasculature system of the body. In an exemplary use, a catheter guiding system or multi-catheter guiding system of the present disclosure can particularly useful for accessing the mitral valve of the heart, and can be used in conjunction with additional treatment devices for performing a variety of mitral valve repair procedures.

Figure 7A:
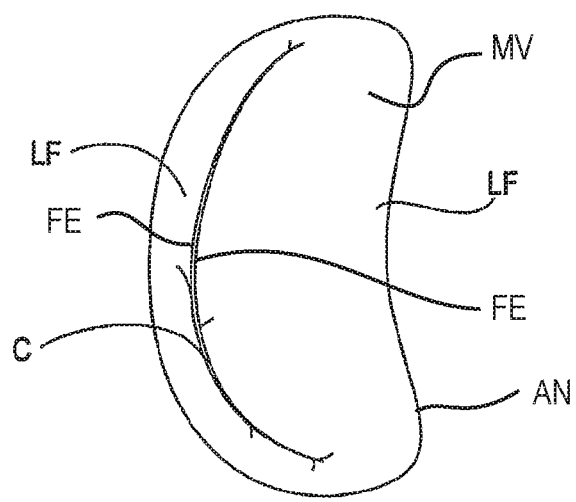
FIGS. 7A-7B illustrate the physiology of a mitral valve.
Figure 7B:
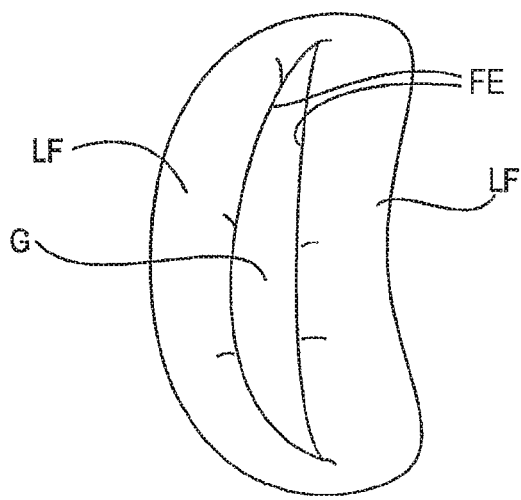

As shown in FIG. 7A, the mitral valve (MV) comprises a pair of leaflets (LF) having free edges (FE) which, in patients with normal heart structure and function, meet evenly to close along a line of coaption (C). The leaflets (LF) attach to the surrounding heart structure along an annular region called the annulus (AN). The free edges (FE) of the leaflets (LF) are secured to the lower portions of the left ventricle LV through chordae tendinae (or "chordae"). As the left ventricle of a heart contracts (which is called "systole"), blood flow from the left ventricle to the left atrium through the mitral valve (MV) (called "mitral regurgitation") is usually prevented by the mitral valve. Regurgitation occurs when the valve leaflets do not close properly and allow leakage from the left ventricle into the left atrium. A number of heart structural defects can cause mitral regurgitation. FIG. 7B shows a mitral valve with a defect causing regurgitation through a gap (G).

Figure 8A:
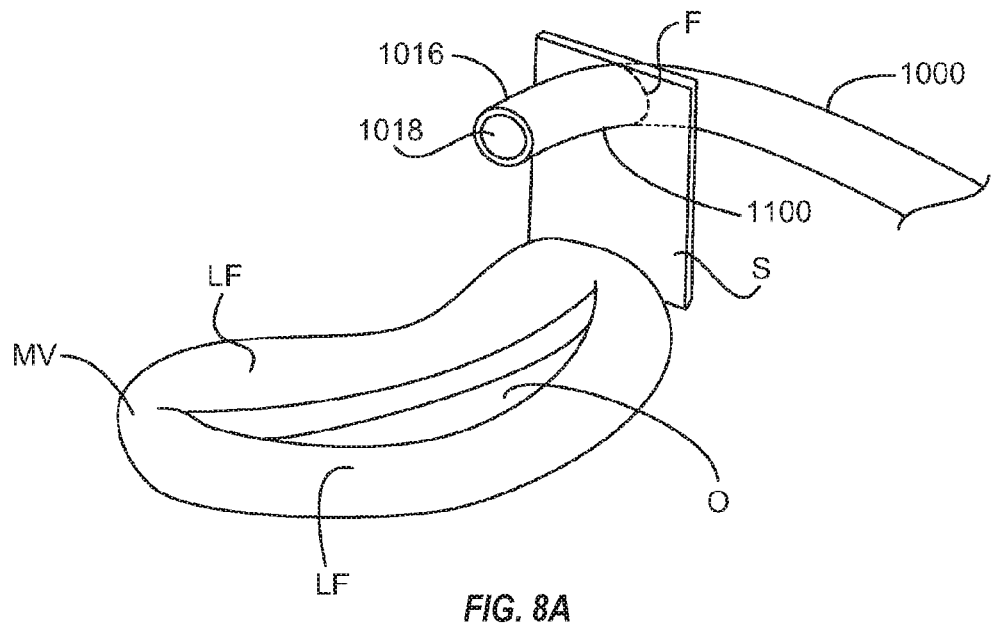
FIGS. 8A-8D illustrate an exemplary use of a steerable guide catheter and multi-catheter system in a mitral valve repair procedure.

FIGS. 8A-8D illustrate a method of using the system for accessing the mitral valve MV. To gain access to the mitral valve, the outer guide catheter 1000 may be tracked over a dilator and guidewire from a puncture in the femoral vein, through the inferior vena cava and into the right atrium. As shown in FIG. 8A, the outer guide catheter 1000 may be punctured through a fossa F in the interatrial septum S. The outer guide catheter 1000 is then advanced through the fossa F and curved by the primary curve 1100 so that the distal end 1016 is directed over the mitral valve MV. It may be appreciated that this approach serves merely as an example and other approaches may be used, such as through the jugular vein, femoral artery, port access or direct access, to name a few.

Positioning of the distal end 1016 over the mitral valve MV may be accomplished by steering of the outer guide catheter 1000 to the desired position. In this example, formation of the primary curve 1100 moves the distal end 1016 within a primary plane, substantially parallel to the valve surface. This moves the distal end 1016 laterally along the short axis of the mitral valve MV, and allows the distal end 1016 to be centered over the opening O between the leaflets LF.

Figure 8B:
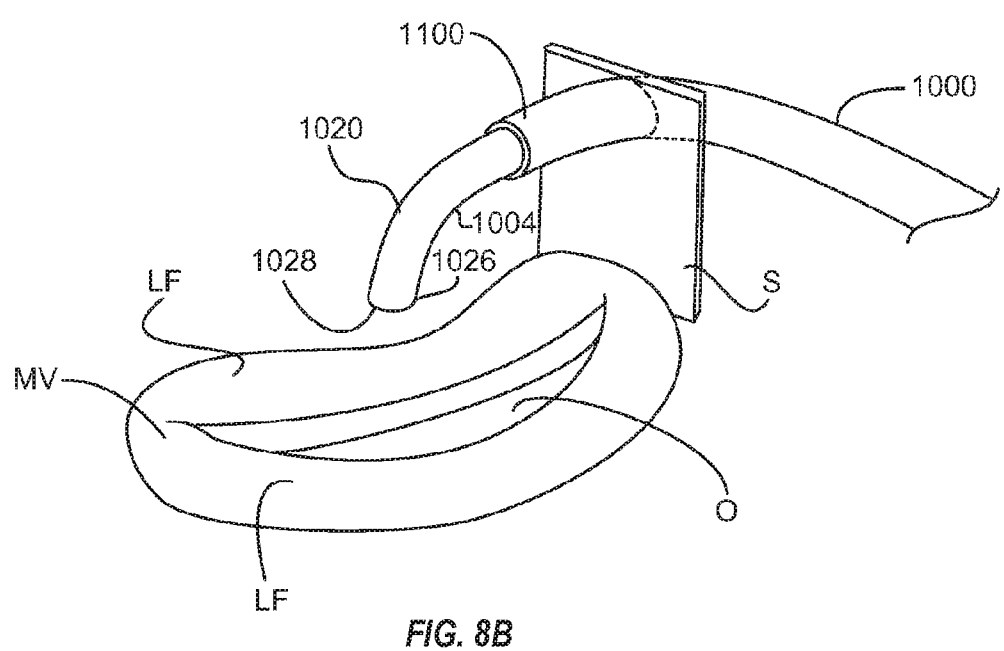

Referring to FIG. 8B, the inner guide catheter 1020 is advanced through the central lumen 1018 of the outer guide catheter 1000 and the distal end 1026 is positioned so that the central lumen 1028 is directed toward the target tissue, the mitral valve MV. In particular, the central lumen 1028 is to be directed toward a specific area of the mitral valve MV, such as toward the opening O between the valve leaflets LF, so that a particular interventional procedure may be performed.

In FIG. 8B, the inner guide catheter 1020 is shown in a position which includes a secondary curve 1104 in a secondary plane. Formation of the secondary curve 1104 moves the distal end 1026 vertically and angularly between the commissures, directing the central lumen 1028 toward the mitral valve MV. In this position an interventional device or catheter 1030 which is passed through the central lumen 1028 would be directed toward and/or through the opening O. Although the primary curve 1100 and the secondary curve 1104 may be varied to accommodate different anatomical variations of the valve MV and different surgical procedures, further adjustment may be desired beyond these two curvatures for proper positioning of the system.

Figure 8C:
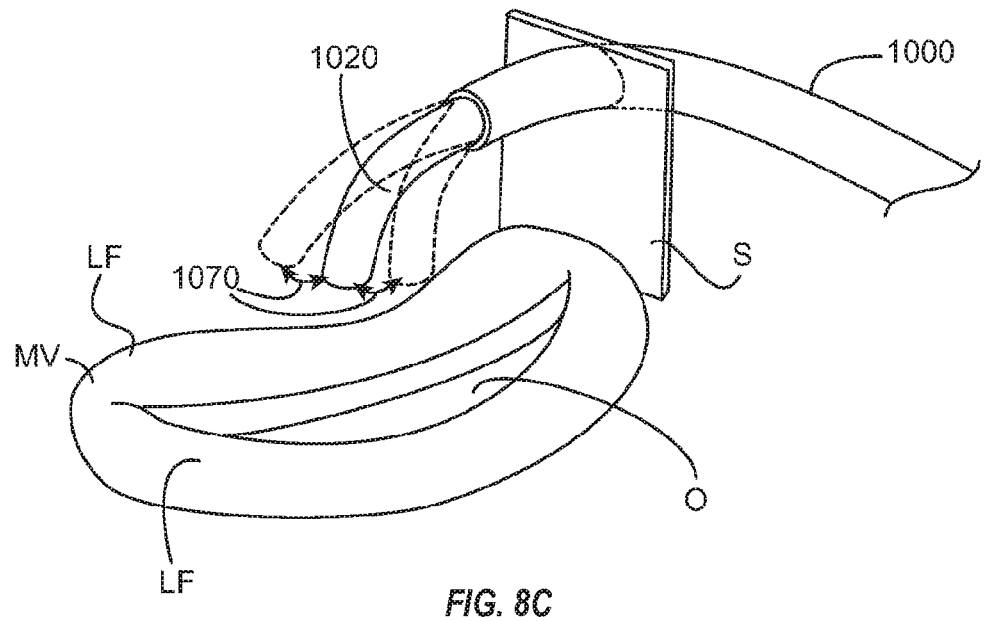

Referring to FIG. 8C, the distal end 1026 of the inner guide catheter 1020 may be positioned through an angle theta 1070. This moves the distal end 1026 vertically and angularly through a theta plane. Movement of the distal end 1026 through the angle theta 1070 in either direction is shown in dashed line in FIG. 12C. Such movement can be achieved by precurvature and/or by steering of the catheter 1020. Consequently, the central lumen 1028 can be directed toward the mitral valve MV within a plane which differs from the secondary plane. After such movements, the inner guide catheter 1020 will be in a position so that the opening of the central lumen 1028 at the end 1016 faces the desired direction. In this case, the desired direction is toward the center of and orthogonal to the mitral valve.

Figure 8D:
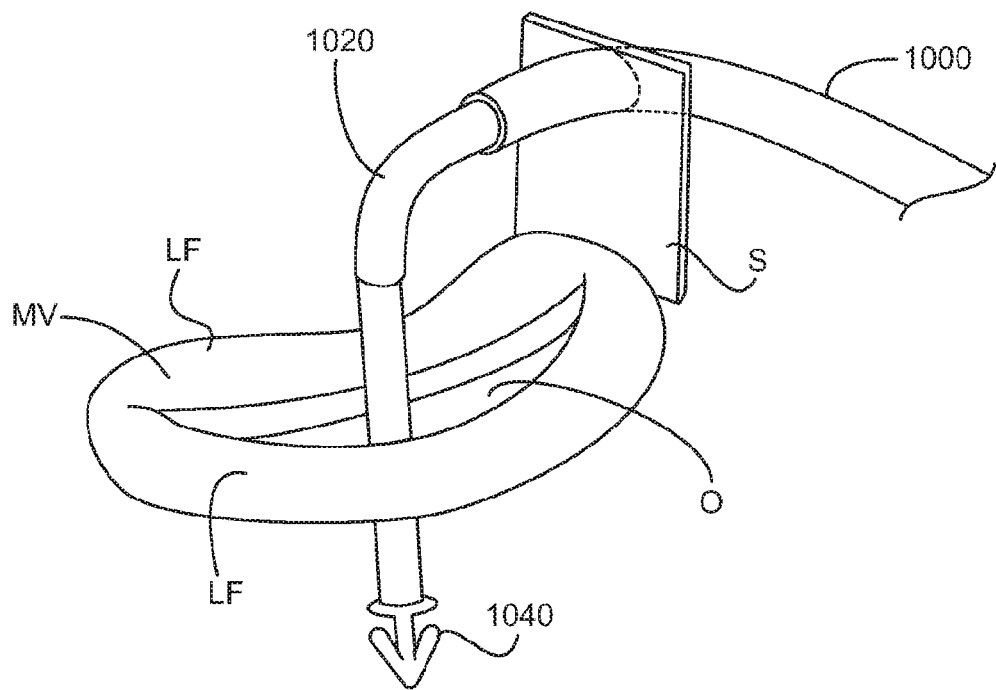

When the curvatures in the catheters 1000, 1020 are formed by steering mechanisms, the steering mechanisms may be locked in place by a locking feature. Locking can provide additional stiffness and stability in the guiding system for the passage of interventional devices or catheters 1030 therethrough, as illustrated in FIG. 4. The interventional catheter 1030 can be passed through the central lumen 1028 toward the target tissue, in this case the mitral valve MV. Positioning of the distal end 1026 over the opening O, as described above, allows the catheter 1030 to pass through the opening O between the leaflets LF if desired, as shown in FIG. 8D. At this point, any desired procedure may be applied to the mitral valve for correction of regurgitation or any other disorder.

V. Fixation Device

Figure 9A:
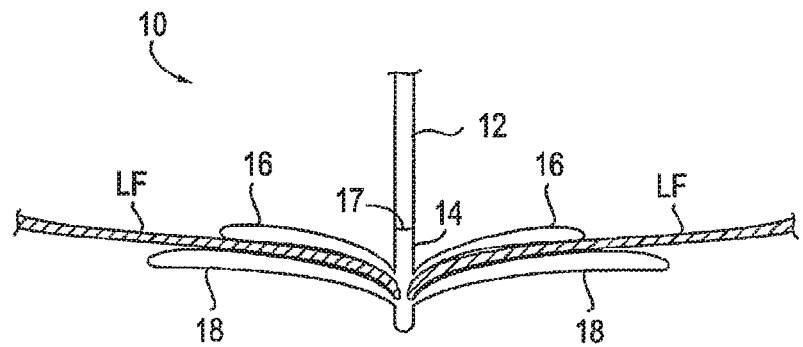
FIGS. 9A-10 illustrate an exemplary tissue fixation device suitable for use with a steerable guide catheter of the present disclosure.

FIGS. 9A-9C and FIG. 10 illustrate an embodiment of a fixation device that may be included in a steerable guide catheter system of the present disclosure. FIG. 9A illustrates a schematic of an interventional tool 10 with a delivery shaft 12 and a fixation device 14. The tool 10 has approached the mitral valve MV from the atrial side and grasped the leaflets LF. The fixation device 14 is releasably attached to the shaft 12 of the interventional tool 10 at the distal end of the shaft 12. In this application, when describing devices, "proximal" means the direction toward the end of the device to be manipulated by the user outside the patient's body, and "distal" means the direction toward the working end of the device that is positioned at the treatment site and away from the user. When describing the mitral valve, proximal means the atrial side of the leaflets and distal means the ventricular side of the leaflets. The fixation device 14 comprises proximal elements 16 and distal elements 18 which protrude radially outward and are positionable on opposite sides of the leaflets LF as shown so as to capture or retain the leaflets therebetween. The fixation device 14 is coupleable to the shaft 12 by a coupling mechanism 17.

Figure 9B:
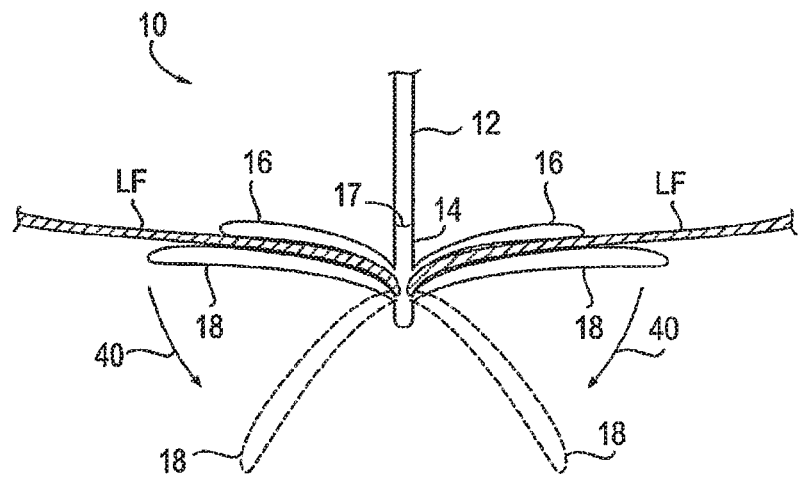
Figure 9C:
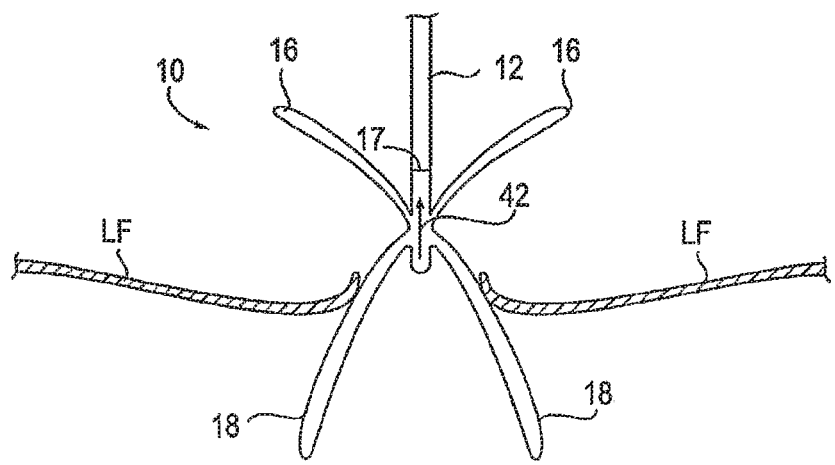

FIG. 9B illustrates that the distal elements 18 may be moved in the direction of arrows 40 to an inverted position. The proximal elements 16 may be raised as shown in FIG. 9C. In the inverted position, the device 14 may be repositioned and then be reverted to a grasping position against the leaflets as in FIG. 9A. Or, the fixation device 14 may be withdrawn (indicated by arrow 42) from the leaflets as shown in FIG. 9C. Such inversion reduces trauma to the leaflets and minimizes any entanglement of the device with surrounding tissues.

Figure 10:
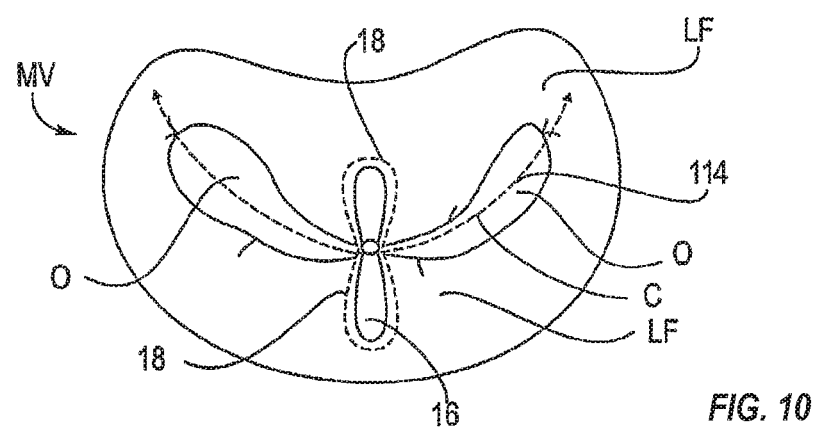

FIG. 10 illustrates the fixation device 14 in a desired orientation in relation to the leaflets LF. The mitral valve MV is viewed from the atrial side, so the proximal elements 16 are shown in solid line and the distal elements 18 are shown in dashed line. The proximal and distal elements 16, 18 are positioned to be substantially perpendicular to the line of coaptation C. During diastole (when blood is flowing from the left atrium to the left ventricle), fixation device 14 holds the leaflets LF in position between the elements 16, 18 surrounded by openings or orifices O which result from the diastolic pressure gradient, as shown in FIG. 10. Once the leaflets are coapted in the desired arrangement, the fixation device 14 is detached from the shaft 12 and left behind as an implant.

The present invention may be embodied in other specific forms without departing from its spirit or essential characteristics. The described embodiments are to be considered in all respects only as illustrative and not restrictive. In fact, any combination of the features disclosed in any of the foregoing embodiments can be combined. The invention can incorporate any combination of the different features described herein, such that components and elements from one embodiment can be incorporated into or replace elements from any of the other embodiments described herein.

What is claimed is:

1. A method for accessing a target area within a body, the method comprising:
    advancing an outer catheter through an interatrial septum;
    forming a primary curve in a distal portion of the outer catheter to position a distal end of the outer catheter over a mitral valve, the primary curve being disposed within a primary plane;
    advancing an inner catheter from the distal end of the outer catheter; and
    forming a secondary curve in a distal portion of the inner catheter to direct an opening of the inner catheter towards the target area, the secondary curve being within a secondary plane transverse to the primary plane;
    advancing an interventional tool toward the mitral valve to access the target area,
    wherein, forming at least one of the primary curve and the secondary curve comprises tensioning a pullwire over a saddle protruding from within an indentation formed at a distal surface of a catheter tip ring, the pullwire extending proximally from a first opening formed in a first inclined surface of the saddle and from a second opening formed in a second inclined surface of the saddle.

2. The method of claim 1, wherein forming the primary curve comprises forming the primary curve substantially parallel to a surface of the mitral valve by tensioning the pullwire disposed within a lumen of the outer catheter.

3. The method of claim 1, wherein positioning the distal end of the outer catheter over the mitral valve comprises moving the distal end laterally along a short axis of the mitral valve by tensioning the pullwire disposed within a lumen of the outer catheter.

4. The method of claim 1, wherein directing the opening of the inner catheter towards the target area comprises directing the opening towards an opening between valve leaflets of the mitral valve by tensioning the pullwire disposed within a lumen of the inner catheter.

5. The method of claim 1, wherein advancing the inner catheter is accomplished without rotation of the inner catheter relative to the outer catheter.

6. The method of claim 1, wherein advancing the inner catheter from the distal end of the outer catheter comprises advancing a keying feature provided on one of the inner catheter and the outer catheter along a complementary keyway on the other of the inner catheter and the outer catheter.

7. The method of claim 1, wherein advancing the inner catheter from the distal end of the outer catheter comprises manipulating at least one steering actuator associated with a proximal handle.

8. A method for accessing a target area within a body, the method comprising:
- advancing an outer catheter toward the target area, the outer catheter having a lumen therethrough;
- forming a primary curve in the outer catheter;
- advancing an inner catheter from an end of the lumen of the outer catheter;
- forming a secondary curve in the inner catheter;
- wherein forming at least one of the primary curve or the secondary curve is accomplished using a tip ring attached to a distal end of the outer catheter or the inner catheter, the tip ring having a distal surface with a first indentation in the distal surface, a first saddle formed within the first indentation and having a first inclined surface and a second inclined surface extending distally to an apex of the saddle that is equal to or proximal the distal surface having the first indentation, a first pullwire channel extends proximally from a first opening formed in the first inclined surface and a second pullwire channel extends proximally from a second opening formed in the second inclined surface.

9. The method of claim 8, wherein advancing the inner catheter through the lumen of the outer catheter comprises advancing a key provided on one of the inner catheter and the outer catheter along a complementary keyway on the other of the inner catheter and the outer catheter.

10. The method of claim 9, wherein the key has a hygroscopicity such that moisture absorption of the key in physiological conditions is 1 percent or less by weight.

11. The method of claim 9, wherein the key is formed at least partially from a polyamide, polyether, or a copolymer of ether and amide units.

12. The method of claim 11, wherein the key further comprises a glass microstructure filler.

13. The method of claim 12, wherein the glass microstructures are glass microspheres.

14. The method of claim 13, wherein the glass microspheres are included in the key in an amount of about 10 percent to about 40 percent by weight.

15. The method of claim 13, wherein the glass microspheres have a diameter within a range selected from about 5 microns to about 15 microns.

16. A method for accessing a target area within a body, the method comprising:
- advancing an outer catheter toward the target area, the outer catheter having a lumen therethrough;
- forming a primary curve in the outer catheter;
- advancing an inner catheter through the lumen of the outer catheter;
- forming a secondary curve in the inner catheter;
- wherein forming at least one of the primary curve or the secondary curve is accomplished using a tip ring attached to a distal end of the outer catheter or the inner catheter, the tip ring having a first saddle configured to engage with a first pullwire, the first pullwire configured to engage with the first saddle upon application of tension to the first pullwire, the application of tension to the first pullwire thereby forming the primary curve or secondary curve, the first pullwire extending proximally from a first opening formed in a first inclined surface of the first saddle and from a second opening formed in a second inclined surface of the first saddle, the first opening and the second opening being disposed on opposite sides of an apex of the first side to which the first inclined surface and the second inclined surface extend.

17. The method of claim 16, wherein advancing the inner catheter is accomplished without rotation of the inner catheter relative to the outer catheter by providing a keying feature, the keying feature including a key joined to the inner catheter or outer catheter, the key formed at least partially from a polyamide and a glass microstructure filler, and a corresponding keyway disposed opposite the key and configured to receive the key.

18. The method of claim 17, wherein forming the primary curve comprises forming the primary curve within the primary curve that is substantially parallel to a surface of a mitral valve by tensioning the first pullwire disposed within a lumen of the outer catheter.

19. The method of claim 17, further comprising positioning the distal end of the outer catheter over a mitral valve comprises moving the distal end laterally along a short axis of a mitral valve by tensioning a pullwire disposed within a lumen of the outer catheter.

20. The method of claim 17, wherein at least one of the inner catheter and the outer catheter comprises a precurve to aid with positioning the distal end.

* * * * *